(12) United States Patent
Wong et al.

(10) Patent No.: US 9,056,098 B2
(45) Date of Patent: Jun. 16, 2015

(54) HEMOGLOBIN-BASED OXYGEN CARRIER-CONTAINING PHARMACEUTICAL COMPOSITION FOR CANCER TARGETING TREATMENT AND PREVENTION OF CANCER RECURRENCE

(71) Applicant: Vision Global Holdings Ltd., Hong Kong (HK)

(72) Inventors: Bing Lou Wong, Irvine, CA (US); Norman Fung Man Wai, Vancouver (CA); Sui Yi Kwok, Hong Kong (HK); Sze Hang Lau, Hong Kong (HK)

(73) Assignee: VISION GLOBAL HOLDINGS LTD., Sheung Wan (HK)

( * ) Notice: Subject to any disclaimer, the term of this patent is extended or adjusted under 35 U.S.C. 154(b) by 0 days.

(21) Appl. No.: 14/308,725

(22) Filed: Jun. 19, 2014

(65) Prior Publication Data

US 2014/0303085 A1    Oct. 9, 2014

Related U.S. Application Data

(63) Continuation of application No. 13/713,031, filed on Dec. 13, 2012, now abandoned.

(51) Int. Cl.
| | |
|---|---|
| A61K 38/00 | (2006.01) |
| A61P 35/00 | (2006.01) |
| A61P 35/04 | (2006.01) |
| A61K 38/42 | (2006.01) |
| A61K 45/06 | (2006.01) |
| A61K 33/38 | (2006.01) |
| A61K 31/513 | (2006.01) |
| A61K 38/05 | (2006.01) |
| A61N 5/00 | (2006.01) |

(52) U.S. Cl.
CPC ............... *A61K 38/42* (2013.01); *A61K 45/06* (2013.01); *A61K 33/38* (2013.01); *A61K 31/513* (2013.01); *A61K 38/05* (2013.01); *A61N 5/00* (2013.01)

(58) Field of Classification Search
None
See application file for complete search history.

(56) References Cited

U.S. PATENT DOCUMENTS 7,932,356 B1 * 4/2011 Wong et al. .............. 530/385
8,377,868 B2   2/2013 Winslow et al.
2010/0311657 A1  12/2010 Abuchowski et al.
2011/0256225 A1  10/2011 Ghoroghchian et al.
2011/0319332 A1  12/2011 Wong et al.

OTHER PUBLICATIONS

Kinghorn et al, Discovery of Natural Product Anticancer Agents from Biodiverse Organisms, Curr Opin Drug Discov Devel. Mar. 2009 ; 12(2): 189-196.*
Gburek et al, Megalin and Cubilin are Endocytic Receptors Involved in Renal Clearance of Hemoglobin, J Am Soc Nephrol 13: 423-430, 2002.*
Verroust et al, Megalin and cubilin—the story of two multipurpose receptors unfolds, Nephrol Dial Transplant (2002) 17: 1867-1871.*
Rowling et al, Megalin-Mediated Endocytosis of Vitamin D Binding Protein Correlates with 25-Hydroxycholecalciferol Actions in Human Mammary Cells, J Nutr. Nov. 2006 ; 136(11): 2754-2759.*
Mandal et al, Mass spectrometric studies of cisplatin-induced changes of hemoglobin, Rapid Commun. Mass Spectrom. 2003; 17: 2748-2754.*
Clinical Trial NCT00398385 (Apr. 2008).*
Waris et al, Reactive oxygen species: role in the development of cancer and various chronic conditions, Journal of Carcinogenesis 2006, 5:14.*
Ketcham, E. M. et al, "Hemoglobin-Based Oxygen Carriers: Development and Clinical Potential", Annals of Emergency Medicine, 1999, vol. 33, p. 326-337.
International Search Report of PCT/US2013/064418 dated Jan. 16, 2014.

* cited by examiner

*Primary Examiner* — Karlheinz R Skowronek
*Assistant Examiner* — Sergio Coffa
(74) *Attorney, Agent, or Firm* — Ella Cheong Hong Kong; Sam T. Yip

(57) ABSTRACT

The present invention provides a pharmaceutical composition containing a hemoglobin-based oxygen carrier for treating cancer, preventing recurrence and metastasis of cancerous tumor. The composition can be used alone or in combination with at least one chemotherapeutic agent such as 5FU, Bortezomib, doxorubicin, cisplatin, or any combination thereof. The hemoglobin-based oxygen carrier in the composition is capable of targeting a surface receptor expressed on cancerous cells and facilitating the uptake of both hemoglobin-based oxygen carrier and the chemotherapeutic agent by the cancerous cells via a receptor-mediated mechanism. The hemoglobin-based oxygen carrier inhibits the expression of hypoxic response elements such as HIF1 α, VEGF, ET1, VHL, etc. The pharmaceutical composition of the present invention is also useful for inducing the apoptosis or cell death of a type of self-renewing and tumor-initiating cells called cancer stem cells which are located in the hypoxic niche of a cancerous tumor.

16 Claims, 32 Drawing Sheets

(A)

(B)

A

B

*Hb= heat stable tetrameric hemoglobin (A) Day 0  (B) Day 3  (C) Day 6  (D) Day 9 - Day 20

(E) Control

SEQUENCE LISTING

```
<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: DNA primer

<400> SEQUENCE: 1
ggcgcgaacg acaagaaaaa g                                              21

<210> SEQ ID NO 2
<211> LENGTH: 23
<212> TYPE: DNA
<213> ORGANISM: Artificial Sequence
<220> FEATURE:
<223> OTHER INFORMATION: DNA primer

<400> SEQUENCE: 2
ccttatcaag atgcgaactc aca                                            23
```

```
<210> SEQ ID NO 3
<211> LENGTH: 20
<212> TYPE: DNA
<213> ORGANISM: Artificial Sequence
<220> FEATURE:
<223> OTHER INFORMATION: DNA primer

<400> SEQUENCE: 3
cagagcagga aaaggagtca                                                   20

<210> SEQ ID NO 4
<211> LENGTH: 20
<212> TYPE: DNA
<213> ORGANISM: Artificial Sequence
<220> FEATURE:
<223> OTHER INFORMATION: DNA primer

<400> SEQUENCE: 4
agtagctgca tgatcgtctg                                                   20

<210> SEQ ID NO 5
<211> LENGTH: 24
<212> TYPE: DNA
<213> ORGANISM: Artificial Sequence
<220> FEATURE:
<223> OTHER INFORMATION: DNA primer

<400> SEQUENCE: 5
aatggaatgg agcaaaagac aatt                                              24

<210> SEQ ID NO 6
<211> LENGTH: 22
<212> TYPE: DNA
<213> ORGANISM: Artificial Sequence
<220> FEATURE:
<223> OTHER INFORMATION: DNA primer

<400> SEQUENCE: 6
attgattgcc ccagcagtct ac                                                22

<210> SEQ ID NO 7
<211> LENGTH: 20
<212> TYPE: DNA
<213> ORGANISM: Artificial Sequence
<220> FEATURE:
<223> OTHER INFORMATION: DNA primer

<400> SEQUENCE: 7
gctactgcca tccaatcgag                                                   20

<210> SEQ ID NO 8
<211> LENGTH: 20
<212> TYPE: DNA
<213> ORGANISM: Artificial Sequence
<220> FEATURE:
<223> OTHER INFORMATION: DNA primer

<400> SEQUENCE: 8
ctctcctatg tgctggcctt                                                   20

<210> SEQ ID NO 9
<211> LENGTH: 21
<212> TYPE: DNA
<213> ORGANISM: Artificial Sequence
<220> FEATURE:
<223> OTHER INFORMATION: DNA primer
```

```
<400> SEQUENCE: 9
ctctctccct catcggtgac a                                              21

<210> SEQ ID NO 10
<211> LENGTH: 22
<212> TYPE: DNA
<213> ORGANISM: Artificial Sequence
<220> FEATURE:
<223> OTHER INFORMATION: DNA primer

<400> SEQUENCE: 10
ggagggcaga gctgagtgtt ag                                             22

<210> SEQ ID NO 11
<211> LENGTH: 20
<212> TYPE: DNA
<213> ORGANISM: Artificial Sequence
<220> FEATURE:
<223> OTHER INFORMATION: DNA primer

<400> SEQUENCE: 11
actgccatcc aatcgagacc                                                20

<210> SEQ ID NO 12
<211> LENGTH: 24
<212> TYPE: DNA
<213> ORGANISM: Artificial Sequence
<220> FEATURE:
<223> OTHER INFORMATION: DNA primer

<400> SEQUENCE: 12
gatggctgaa gatgtactcg atct                                           24

<210> SEQ ID NO 13
<211> LENGTH: 23
<212> TYPE: DNA
<213> ORGANISM: Artificial Sequence
<220> FEATURE:
<223> OTHER INFORMATION: DNA primer

<400> SEQUENCE: 13
acaacaaatt caggtacgct gtg                                            23

<210> SEQ ID NO 14
<211> LENGTH: 24
<212> TYPE: DNA
<213> ORGANISM: Artificial Sequence
<220> FEATURE:
<223> OTHER INFORMATION: DNA primer

<400> SEQUENCE: 14
tctgatcaat gtcatgagca aagg                                           24

<210> SEQ ID NO 15
<211> LENGTH: 20
<212> TYPE: DNA
<213> ORGANISM: Artificial Sequence
<220> FEATURE:
<223> OTHER INFORMATION: DNA primer

<400> SEQUENCE: 15
gttctcaagg cacaggtctc                                                20

<210> SEQ ID NO 16
```

```
<211> LENGTH: 23
<212> TYPE: DNA
<213> ORGANISM: Artificial Sequence
<220> FEATURE:
<223> OTHER INFORMATION: DNA primer

<400> SEQUENCE: 16
gcaggtcact tatgtcactt atc                                              23

<210> SEQ ID NO 17
<211> LENGTH: 20
<212> TYPE: DNA
<213> ORGANISM: Artificial Sequence
<220> FEATURE:
<223> OTHER INFORMATION: DNA primer

<400> SEQUENCE: 17
tgccaagcag gaaaagaact                                                  20

<210> SEQ ID NO 18
<211> LENGTH: 20
<212> TYPE: DNA
<213> ORGANISM: Artificial Sequence
<220> FEATURE:
<223> OTHER INFORMATION: DNA primer

<400> SEQUENCE: 18
tttgacgctg tttctcatgg                                                  20

<210> SEQ ID NO 19
<211> LENGTH: 20
<212> TYPE: DNA
<213> ORGANISM: Artificial Sequence
<220> FEATURE:
<223> OTHER INFORMATION: DNA primer

<400> SEQUENCE: 19
ttcagacaga gccaaggtgc                                                  20

<210> SEQ ID NO 20
<211> LENGTH: 21
<212> TYPE: DNA
<213> ORGANISM: Artificial Sequence
<220> FEATURE:
<223> OTHER INFORMATION: DNA primer

<400> SEQUENCE: 20
caatgacatc aactgggcaa t                                                21

<210> SEQ ID NO 21
<211> LENGTH: 23
<212> TYPE: DNA
<213> ORGANISM: Artificial Sequence
<220> FEATURE:
<223> OTHER INFORMATION: DNA primer

<400> SEQUENCE: 21
ggcagtcaag cacttttctg tag                                              23

<210> SEQ ID NO 22
<211> LENGTH: 21
<212> TYPE: DNA
<213> ORGANISM: Artificial Sequence
<220> FEATURE:
<223> OTHER INFORMATION: DNA primer

<400> SEQUENCE: 22
```

```
gtcaaccaca ccacggataa a                                                    21

<210> SEQ ID NO 23
<211> LENGTH: 20
<212> TYPE: DNA
<213> ORGANISM: Artificial Sequence
<220> FEATURE:
<223> OTHER INFORMATION: DNA primer

<400> SEQUENCE: 23
attagcatgg cggcacacat                                                      20

<210> SEQ ID NO 24
<211> LENGTH: 22
<212> TYPE: DNA
<213> ORGANISM: Artificial Sequence
<220> FEATURE:
<223> OTHER INFORMATION: DNA primer

<400> SEQUENCE: 24
tggagtgcag tggcatactc at                                                   22
```

HEMOGLOBIN-BASED OXYGEN CARRIER-CONTAINING PHARMACEUTICAL COMPOSITION FOR CANCER TARGETING TREATMENT AND PREVENTION OF CANCER RECURRENCE

CROSS-REFERENCE TO RELATED APPLICATIONS

The present application is a continuation application of U.S. non-provisional patent application Ser. No. 13/713,031 filed Dec. 13, 2012, which claims priority from the U.S. provisional patent application Ser. No. 61/712,853 filed Oct. 12, 2012, and the disclosure of which are incorporated herein by reference.

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the processes, experiments, and data as described below and in the drawings attached hereto: Copyright © 2012-2014, Vision Global Holdings Limited, All Rights Reserved.

TECHNICAL FIELD

The present invention relates to a hemoglobin-based oxygen carrier-containing pharmaceutical composition for cancer targeting treatment and prevention of tumor recurrence in humans and other animals. In particular, the present invention relates to a composition including a hemoglobin-based oxygen carrier which is either administered alone or in combination with at least one chemotherapeutic agent for treating cancers, targeting cancerous cells/cancer stem cells/tissues containing any of these cells, and preventing the recurrence of tumors.

BACKGROUND OF INVENTION

Hemoglobin plays an important role in most vertebrates for gaseous exchange between the vascular system and tissue. It is responsible for carrying oxygen from the respiratory system to the body cells via blood circulation and also carrying the metabolic waste product carbon dioxide away from body cells to the respiratory system, where the carbon dioxide is exhaled. Since hemoglobin has this oxygen transport feature, it can be used as a potent oxygen supplier if it can be stabilized ex vivo and used in vivo.

Naturally-occurring hemoglobin is a tetramer which is generally stable when present within red blood cells. However, when naturally-occurring hemoglobin is removed from red blood cells, it becomes unstable in plasma and splits into two α-β dimers. Each of these dimers is approximately 32 kDa in molecular weight. These dimers may cause substantial renal injury when filtered through the kidneys and excreted. The breakdown of the tetramer linkage also negatively impacts the sustainability of the functional hemoglobin in circulation.

In order to solve the problem, recent developments in hemoglobin processing have incorporated various cross-linking techniques to create intramolecular bonds within the tetramer as well as intermolecular bonds between the tetramers to form polymeric hemoglobin.

Hypoxia is common in cancers. Hypoxia can lead to ionizing radiation and chemotherapy resistance by depriving tumor cells of the oxygen essential for the cytotoxic activities of these agents. Hypoxia may also reduce tumor sensitivity to radiation therapy and chemotherapy through one or more indirect mechanisms that include proteomic and genomic changes. Therefore, there is a need for improved cancer-treatment compositions, particularly, improved cancer-treatment compositions that enhance the efficacy of cytotoxic agents.

Although tumor metastasis causes about 90 percent of cancer deaths, the exact mechanism that allows cancer cells to spread from on part of the body to another is not well understood. So, the improved cancer-treatment compositions that prevent the cancer recurrence is important.

Many recent studies have shown that cancer stem cells (CSCs) play an important role in cancer and tumor development. Wang and Dick (2005) revisited the self-renewal and tumor cell proliferating potentials of leukemia stem cells found in tumor by the stochastic model and cancer stem cell model proposed earlier. According to the stochastic model, there is generally one class of tumor cells which are functionally homogeneous, and the genetic changes can lead to malignancy progression in all these tumor cells. In contrast, the cancer stem cell model proposes that a rare population of cells which have a distinct ability to consistently initiate tumor growth and are able to reproduce a hierarchy of functionally heterogeneous classes of cells may have different tumorigenic pathways compared with the majority of the cells in a tumor. The tumor-initiating cells proposed in the cancer stem cell model can be progressively identified and purified from the rest of the cells. These cells are called cancer stem cells (CSCs). Like leukemia stem cells, other cancers such as breast cancer appear to be driven by the rare population of tumor-initiating cells. Two phenotypes of cells have been identified in breast cancer where one minority phenotype is able to form mammary tumors while another phenotype is not. In brain cancer, two types of cells are found: $CD133^+$ cells possess differentiative, self-renewal, and tumor-initiating abilities in vivo whereas $CD133^-$ cells cannot. More and more evidences have been found to support that these cancer stem cells may be at the apex of all neoplastic systems, and thereby become a new target for cancer treatment. A review article (Mohyeldin et al., 2010) suggested that cancer stem cell niches have much lower oxygen tension. A hypoxic niche is found to be located further away from vasculature of a tumor and contains cancer stem cells which differentially respond to hypoxia with distinct HIF (Hypoxia-inducible factors) induction patterns, in particular HIF-2α. It becomes a new target in the signaling pathways that regulate cancer stem cell self-renewal, proliferation, and survival, and the inhibition of which will attenuate their tumor initiation potential.

Thus there is a need in the art for a composition that can provide high oxygen tension in cancer stem cells. Such a composition could be used to produce oxidative stress or shocks which leads to DNA damage and subsequent DNA damage induced apoptosis in the cancer stem cells.

SUMMARY OF INVENTION

The present invention relates to a hemoglobin-based oxygen carrier-containing pharmaceutical composition for targeted treating and preventing recurrence of cancer in humans and other animals. The first aspect of the present invention is to provide a hemoglobin-based oxygen carrier which is configured to target cancerous cells, cancer stem cells (CSCs) and/or cancerous progenitor cells, and/or tissues containing any of these cells in a human or animal body, triggering a receptor-mediated mechanism and leading a combined chemotherapeutic agent to localize together in the cytoplasm of the cancerous cells, CSCs, and/or tissues containing any of these cells, in order to increase the efficacy of both hemoglobin-based oxygen carrier and the chemotherapeutic agent. The localized hemoglobin-based oxygen carrier is also found to sensitize the cancerous cells and CSCs such that the cancerous cells and CSCs become more sensitive to the chemotherapeutic agent. The second aspect of the present invention is to provide a method of using the hemoglobin-based oxygen carrier-containing pharmaceutical composition of the present invention for treating cancer and preventing recurrence of cancer by administering said composition to a subject in need thereof suffering from various tumors, cancers or diseases associated with tumors or cancers.

The hemoglobin-based oxygen carrier used in the present invention can be a heat stable cross-linked tetrameric, polymerized, pegylated or recombinant/modified hemoglobin which is used in combination with at least one chemotherapeutic agent for the treatment of various cancers such as leukemia, head and neck cancer, colorectal cancer, lung cancer, breast cancer, liver cancer, nasopharyngeal cancer, esophageal cancer and brain cancer. The hemoglobin-based oxygen carrier itself is also found to have an ability to destroy cancer cells through improving the oxygenation of tumors in a hypoxic condition, thereby enhancing the sensitivity towards radiation and chemotherapeutic agents.

Moreover, the hemoglobin-based oxygen carrier of the present invention can also be used alone for reducing cancerous tumor recurrence and minimizing tumor cell metastasis. Said hemoglobin is administered prior to ischemia for a tumor removal surgery and during re-establishment of blood supply (reperfusion) upon removal of tumor. The hemoglobin-based oxygen carrier can also be used to increase oxygenation of cancerous tissues and with chemotherapeutic agents then subsequently reducing the size of a tumor. As a result, the hemoglobin-based oxygen carrier-containing composition of the present invention can be administered alone or in combination with at least a chemotherapeutic agent for treating or preventing the recurrence of cancerous tumors.

The method of the present invention also includes using a combination of different chemotherapeutic drugs and/or radiotherapy with the hemoglobin-based oxygen carrier of the present invention to give a synergistic effect on cancer treatment and prevention of tumor recurrence.

The third aspect of the present invention relates to the composition of the present invention for providing oxidative stress or shock to the tumor in order to kill a rare population of self-renewing and tumor-initiating cells known as cancer stem cells. The composition of the present invention for providing high oxygen tension to the tumor includes a hemoglobin-based oxygen carrier which includes tetrameric cross-linked hemoglobin or polymerized hemoglobin, where both of them are prepared to contain an undetectable amount of dimer and low percentage of met-hemoglobin. The hemoglobin-based oxygen carrier in said composition is configured for penetration into the cancerous tissues of the tumor where the cancer stem cells are found to selectively proliferate within the tumor. Said hemoglobin-based oxygen carrier can be used alone or in combination with at least one chemotherapeutic agent including Bortezomib, 5-fluorouracil, doxorubicin, cisplatin, or any combination thereof for oxygenating the tumor and providing oxidative stress or shock to said cancer stem cells in order to induce apoptosis or death of said cancer stem cells, which result in the effect in the treatment of and preventing from the recurrence of cancer or cancerous tumor. The hemoglobin-based oxygen carrier of the present invention is also modified to avoid dissociation into dimer such that it becomes more stable and has a longer half life in the circulation. Unlike the naturally occurring hemoglobin, this longer half life property facilitates the penetration thereof into the target cells including both cancerous cells, cancer stem cells and/or cancer progenitor cells. Similar to the effect on cancer cells, the hemoglobin-based oxygen carrier in the composition of the present invention also sensitize the cancer stem cells to chemotherapeutic agent or radiotherapy. In other words, the composition of the present invention is an effective adjunctive therapy which can be administered prior to or in combination with chemotherapy and/or radiotherapy. In any aspects of the present invention described herein, the hemoglobin-based oxygen carrier can be administered to a subject in needs thereof at a concentration of 9.5 g/dL-10.5 g/dL for the purpose(s) of targeting the cells in the cancerous tissues or tumors, triggering the receptor-mediated mechanism, penetrating and being localized into the cancerous tissue or tumor cells, inducing apoptosis of the cancerous tissue or tumor cells, sensitizing the cells to the chemotherapeutic agent or radiotherapy which is administered concurrently or subsequently, either before, during or after a surgical removal of the cancerous tissue or tumor.

DEFINITIONS

Figure 1:
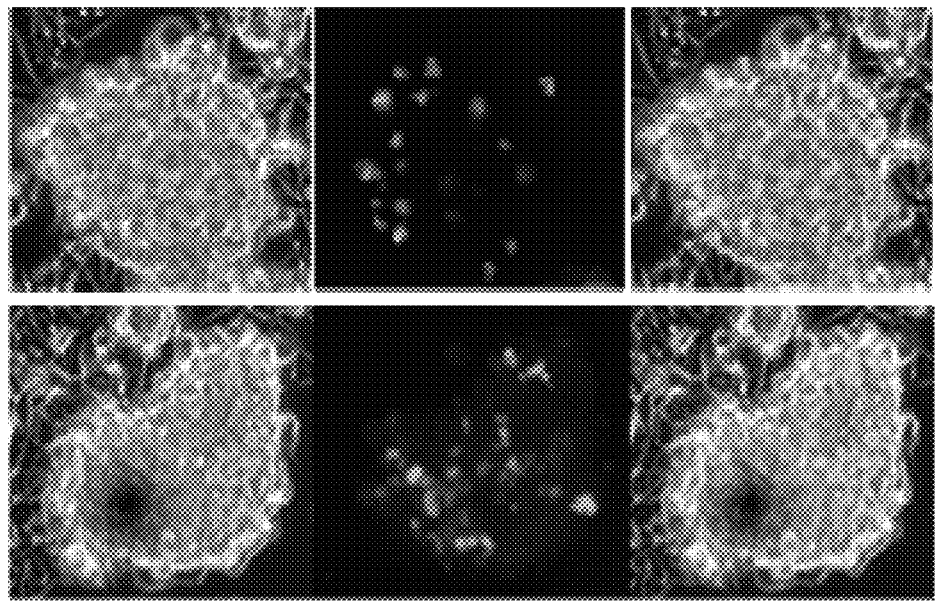
FIG. 1 is a set of microscopic images in the same magnification showing the uptake of (A) fluorescent-labeled heat stable hemoglobin-based oxygen carrier and (B) fluorescent-labeled polymerized hemoglobin into liver cancer cells.
Figure 1:
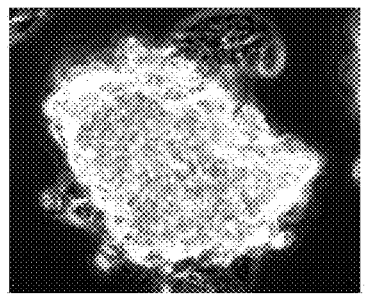

The term "cancer stem cell" refers to the biologically distinct cell within the neoplastic clone that is capable of initiating and sustaining tumor growth in vivo (i.e. the cancer-initiating cell).

"Hb" used herein refers to cross-linked tetrameric hemoglobin which is heat stable with undetectable amount of dimers and low percentage of met-hemoglobin. The heat stable cross-linked tetrameric hemoglobin has a molecular weight of 60-70 kDa which is heat treated and added with 0.05%-0.4% of N-acetyl cysteine during the synthesis. The resulting heat stable cross-linked tetrameric hemoglobin has undetectable amount of dimers and less than 5% of met-hemoglobin. The heat stable cross-linked tetrameric hemoglobin is also free of vasoconstricting impurities and protein impurities, non-pyrogenic, endotoxin-free, phospholipid-free, and stroma-free. The cross-linking within the tetrameric hemoglobin molecule can be between alpha/alpha subunits, alpha/beta subunits or alpha-beta subunits.

"Modified hemoglobin" or "Recombinant hemoglobin" defined herein refers to any natural hemoglobin or purified hemoglobin which is either chemically conjugated with or surface modified with at least one compound. Said compound may include poly(ethylene) glycol (PEG). One of the examples of the modified hemoglobin used in the present invention is pegylated hemoglobin.

DETAILED DESCRIPTION OF INVENTION

Hemoglobin is an iron-containing oxygen-transport protein in red blood cells of the blood of mammals and other animals. Hemoglobin exhibits characteristics of both the tertiary and quaternary structures of proteins. Most of the amino acids in hemoglobin form alpha helices connected by short non-helical segments. Hydrogen bonds stabilize the helical sections inside the hemoglobin causing attractions within the molecule thereto folding each polypeptide chain into a specific shape. A hemoglobin molecule is assembled from four globular protein subunits. Each subunit is composed of a polypeptide chain arranged into a set of α-helix structural segments connected in a "myoglobin fold" arrangement with an embedded heme group.

The heme group consists of an iron atom held in a heterocyclic ring, known as a porphyrin. The iron atom binds equally to all four nitrogen atoms in the center of the ring which lie in one plane. Oxygen is then able to bind to the iron center perpendicular to the plane of the porphyrin ring. Thus a single hemoglobin molecule has the capacity to combine with four molecules of oxygen.

In adult humans, the most common type of hemoglobin is a tetramer called hemoglobin A consisting of two α and two β non-covalently bound subunits designated as α2β2, each made of 141 and 146 amino acid residues respectively. The size and structure of α and β subunits are very similar to each other. Each subunit has a molecular weight of about 16 kDa for a total molecular weight of the tetramer of about 65 kDa. The four polypeptide chains are bound to each other by salt bridges, hydrogen bonds and hydrophobic interaction. The structure of bovine hemoglobin is similar to human hemoglobin (90.14% identity in a chain; 84.35% identity in β chain). The difference is the two sulfhydryl groups in the bovine hemoglobin positioned at β Cys 93, while the sulfhydryls in human hemoglobin are at positioned at α Cys 104, β Cys 93 and β Cys 112 respectively.

In naturally-occurring hemoglobin inside the red blood cells, the association of an a chain with its corresponding β chain is very strong and does not disassociate under physiological conditions. However, the association of one αβ dimer with another αβ dimer is fairly weak outside red blood cells. The bond has a tendency to split into two αβ dimers each approximately 32 kDa. These undesired dimers are small enough to be filtered by the kidneys and be excreted, with the result being potential renal injury and substantially decreased intravascular retention time. Therefore, stabilized cross-linked tetrameric, polymeric and/or recombinant/modified hemoglobin are the important molecule in a pharmaceutical composition for oxygen delivery. The source of hemoglobin can be from, but not limited to, human, bovine, porcine, equine, and canine whole blood.

The pharmaceutical composition of the present invention contains a heat stable hemoglobin-based oxygen carrier which is configured to attach to receptors on tumor cells to facilitate selective targeting of hypoxic tumor cells over normal, non-hypoxic healthy tissue and that can be used in cancer treatment as it can be taken up preferentially into cancer cells. In FIG. 1A, live cell imaging is used to show how the heat-stable tetrameric hemoglobin (Hb) has efficacy against liver cancer. A fluorescently-conjugated Hb is prepared by allowing conjugation between Hb and fluorescein isothiocyanate (FITC) (buffered with $NaHCO_3$ at pH9.3) for 1 hour at room temperature in an enclosed system purged with $N_2$. Subsequent purification is performed to remove unconjugated Hb and free FITC using protein purification columns (Millipore). The freshly conjugated Hb-FITC probe is immediately employed for live cell uptake studies. Liver cancer cells, HepG2, and the metastatic liver cancer cells, Huh7, are exposed to 0.0125 g/dL for 15 min prior to live cell acquisition. The uptake of Hb-FITC into both types of liver cancer cells after 15 min of exposure is observed (FIG. 1A). The uptake of Hb-FITC peaks after 1 hour of exposure (FIG. 1A). Under a hypoxic condition, the monolayer liver cancer cells are observed to curl-up into a three-dimensional structure, and Hb-FITC is detected to be more preferentially taken up by these cancer cells than normal cells. The uptake of polymerized hemoglobin into liver cancer cell is shown in FIG. 1B.

Figure 2:
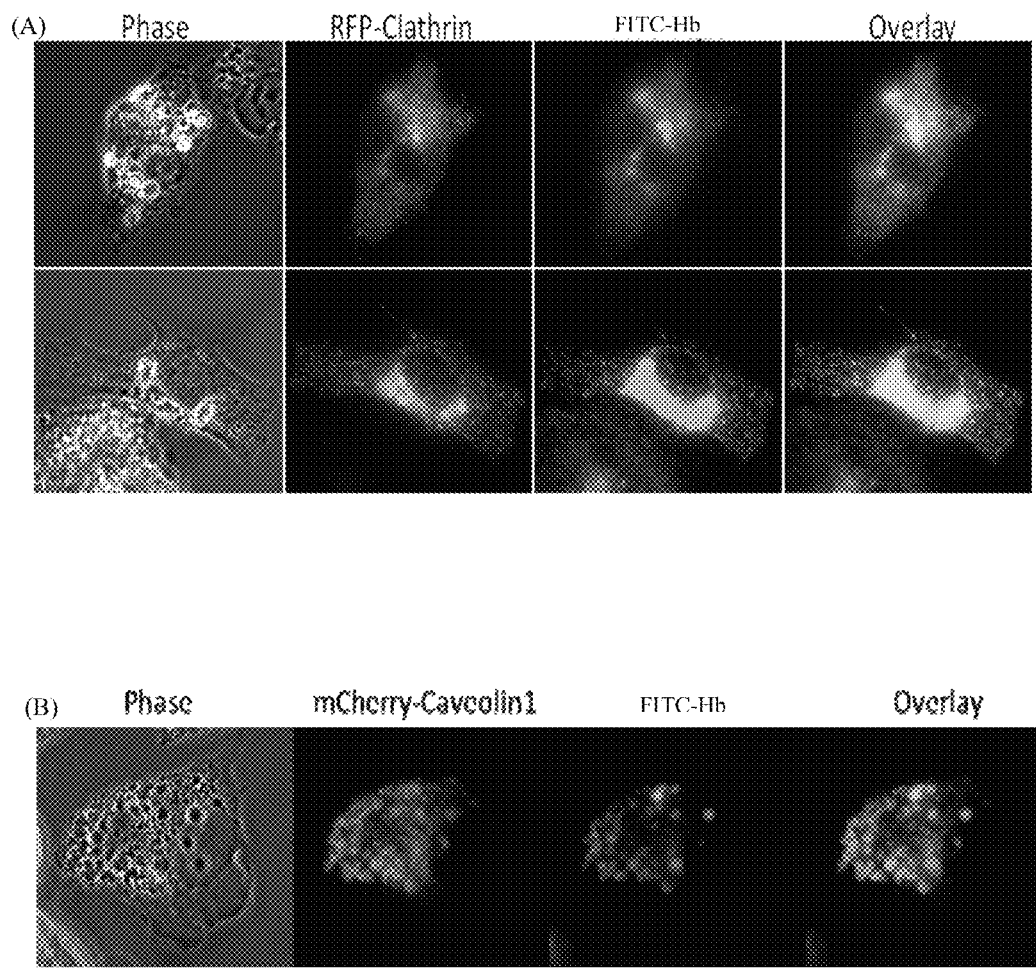
FIG. 2 is two sets of microscopic images in the same magnification showing the uptake of fluorescent-labeled heat stable hemoglobin-based oxygen carrier into liver cancer cells via the Clathrin mediated pathway (upper panel) but not via Caveolin-1 mediated pathway (lower panel).

The ability of cellular uptake of the hemoglobin molecule is through protein-coat vesicular endocytosis. Two common protein coats which could be internalized are Clathrin and Caveolin 1. Red fluorescent protein tagged Clathrin (RFP-Clathrin) and Caveolin 1 (mCherry-Caveolin1) plasmids are constructed, and the plasmids are independently expressed in HepG2 or Huh7 cells taken up with FITC-conjugated Hb. Time lapse imaging studies (FIG. 2) reveals that Hb-FITC colocalizes with RFP-Clathrin, but not mCherry-Caveolin1, suggesting that hemoglobin molecule enters into liver cancer cells through Clathrin-mediated endocytosis.

The efficacy of hemoglobin alone and with adjunctive therapies in non-metastatic and metastatic liver cancer cells is demonstrated in the present invention by studying the $IC_{50}$ of various drugs in two liver cancer models, HepG2 and Huh7, and under both normoxic and hypoxic conditions (the results are shown in TABLE 1). Under normoxic condition, the $IC_{50}$ of Cisplatin, Doxorubicin, Bortezomib, and 5-fluorouracil (5FU) in HepG2 cells are 130 uM, 10 uM, 0.5 uM, and 4 mM respectively, and the $IC_{50}$ of Cisplatin, Doxorubicin, Bortezomib, and 5FU in Huh7 cells are 70 uM, 5 uM, 55 uM, and 3.5 mM respectively. Under hypoxic condition, the $IC_{50}$ of Cisplatin, Doxorubicin, Bortezomib, and 5FU in HepG2 cells are 170 uM, 30 uM, 0.7 uM, and 4 mM respectively, and the $IC_{50}$ of Cisplatin, Doxorubicin, Bortezomib, and 5FU in Huh7 cells are 100 uM, 6 uM, 60 uM, and 4 mM respectively. The 3-(4,5-cimethylthiazol-2-yl)-2,5-diphenyl tetrazolium bromide (MTT) assay result suggests that under normoxic condition, Huh7 cells are more sensitive to Cisplatin and Doxorubicin, but are 110-fold more resistance to Bortezomib as compared to HepG2 cells under normoxic condition (a target drug against the proteasomal subunits PSMB1, 5 and 6). Under hypoxic condition, Huh7 cells become more sensitive to Cisplatin and Doxorubicin, and are also highly resistant to Bortezomib (86-fold) as compared to HepG2 cells under hypoxic condition. The results reveal that metastatic liver cancer cells (Huh7) are generally more resistant to Bortezomib than non-metastatic liver cancer cells (HepG2) notwithstanding under normoxic or hypoxic condition.

TABLE 1

| HepG2 normoxic | | HepG2 hypoxic | |
|---|---|---|---|
| Cisplatin | 130 uM | Cisplatin | 170 uM |
| Doxorubicin | 10 uM | Doxorubicin | 30 uM |
| Bortezomib | 0.5 uM | Bortezomib | 0.7 uM |
| 5FU | 4 mM | 5FU | 4 mM |

TABLE 1-continued

| Huh7 normoxic | | Huh7 hypoxic | |
|---|---|---|---|
| Cisplatin | 70 uM | Cisplatin | 100 uM |
| Doxorubicin | 5 uM | Doxorubicin | 6 uM |
| Bortezomib | 55 uM | Bortezomib | 60 uM |
| 5FU | 3.5 mM | 5FU | 4 mM |

The MTT results also reveal that Hb alone would not cause any cell death. However, significant chemosensitization of 5FU and Bortezomib is observed when administered at their respective $IC_{50}$ together with 0.2 g/dL of Hb. Under normoxic condition, an additional 33% (total 83%) cell death is detected in 5FU and Hb treated HepG2 cells, whereas an additional 20% (total 50%) cell death is observed in Bortezomib and Hb-treated Huh7 cells. Under a hypoxic condition, an additional 42% (total 92%) cell death is detected in Bortezomib and Hb-treated HepG2 cells, while an increment of 35% (total 85%) cell death is observed in 5FU and Hb-treated HepG2 cells. Under the same hypoxic condition, an additional 20% (total 72%) cell death in 5FU and Hb-treated Huh7 cells is observed. 5FU is a pyrimidine analog that inhibits thymidylate synthase. Bortezomib is the first therapeutic proteasome inhibitor used initially for treating myeloma patients. It is reported to cause apoptosis in liver cancer cells (Koschny et AL., Hepatology, 2007). Taken together, hemoglobin molecule is observed to have significant synergistic effects with 5FU and Bortezomib on both non-metastatic and metastatic cancer.

Hypoxia is a common physiological feature of tumors. Intratumoural hypoxia is also common in liver cancer. The condition of hypoxia is known to activate a signaling cascade that results in the stabilization of the hypoxia-inducible factor 1 (HIF1 α) transcription factor and activation of HIF1 α effector genes (over 60 genes) that possess a hypoxia response element (HRE). These HIF1 α downstream effectors are involved in cell survival, adaptation, anaerobic metabolism, immune reaction, cytokine production, vascularization and general tissue homeostasis.

Figure 3:
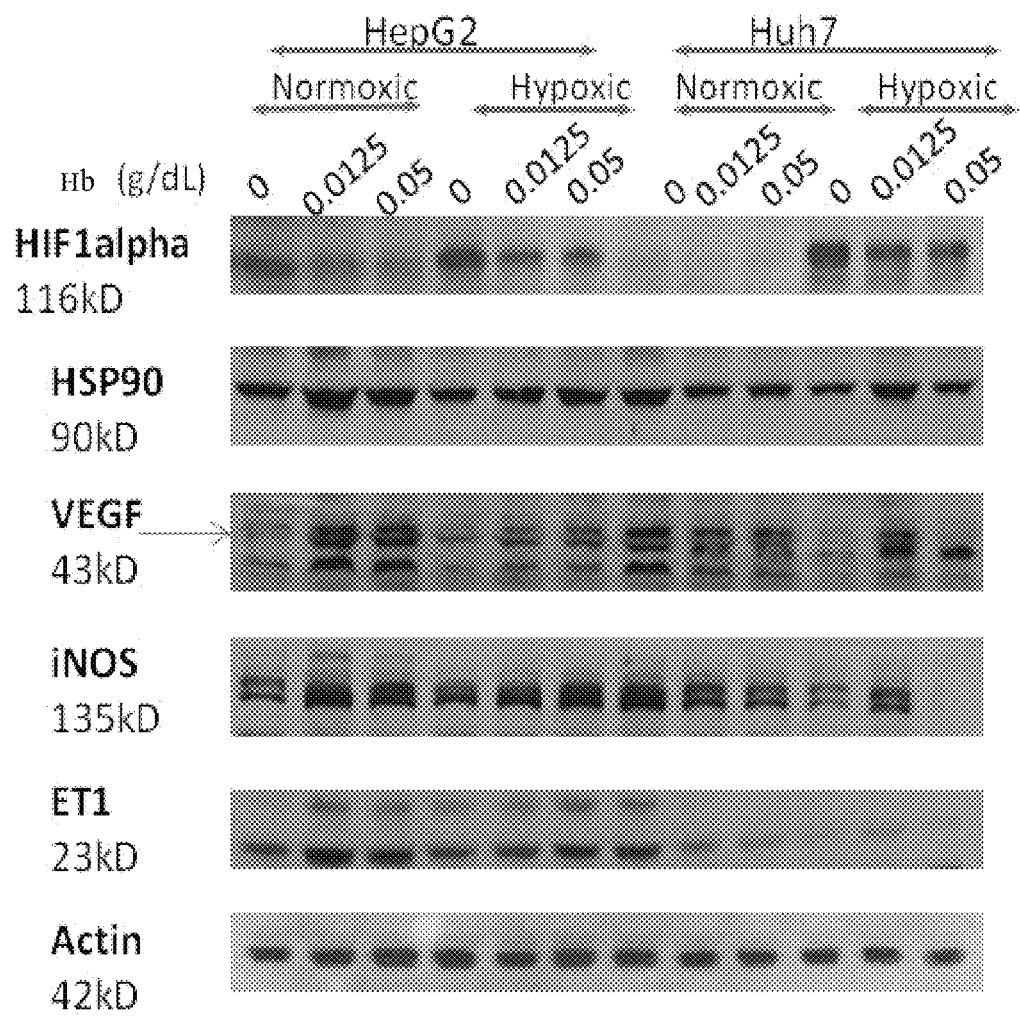
FIG. 3 shows the expression of different proteins in liver cancer cells after treating with the heat stable hemoglobin-based oxygen carrier in different concentrations.
Figure 4:
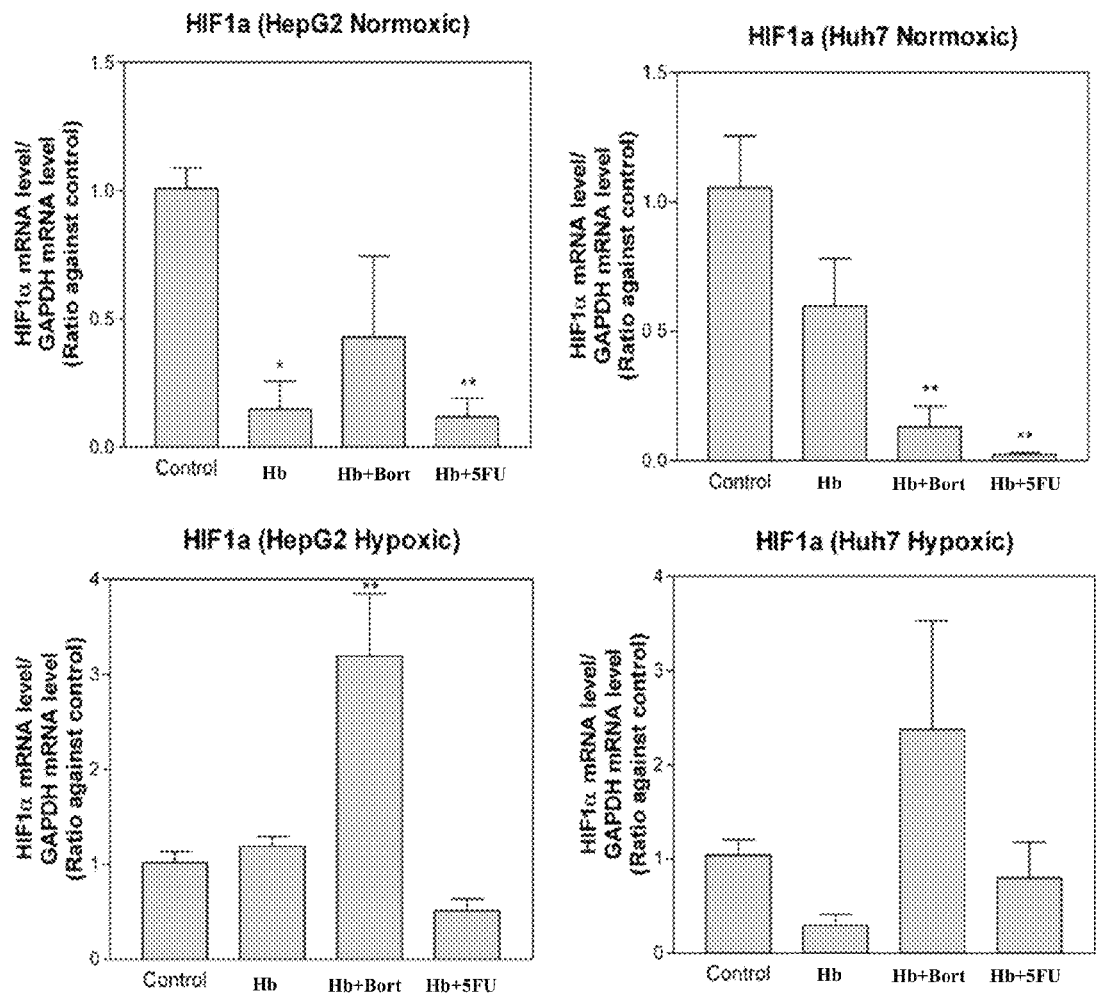
FIG. 4 shows the expression of hypoxia-inducible factor 1 (HIF1 α) gene in liver cancer cells (HepG2 and Huh7) after treating with different concentrations of heat stable hemoglobin-based oxygen carrier and under normoxic vs hypoxic conditions.
Figure 8:
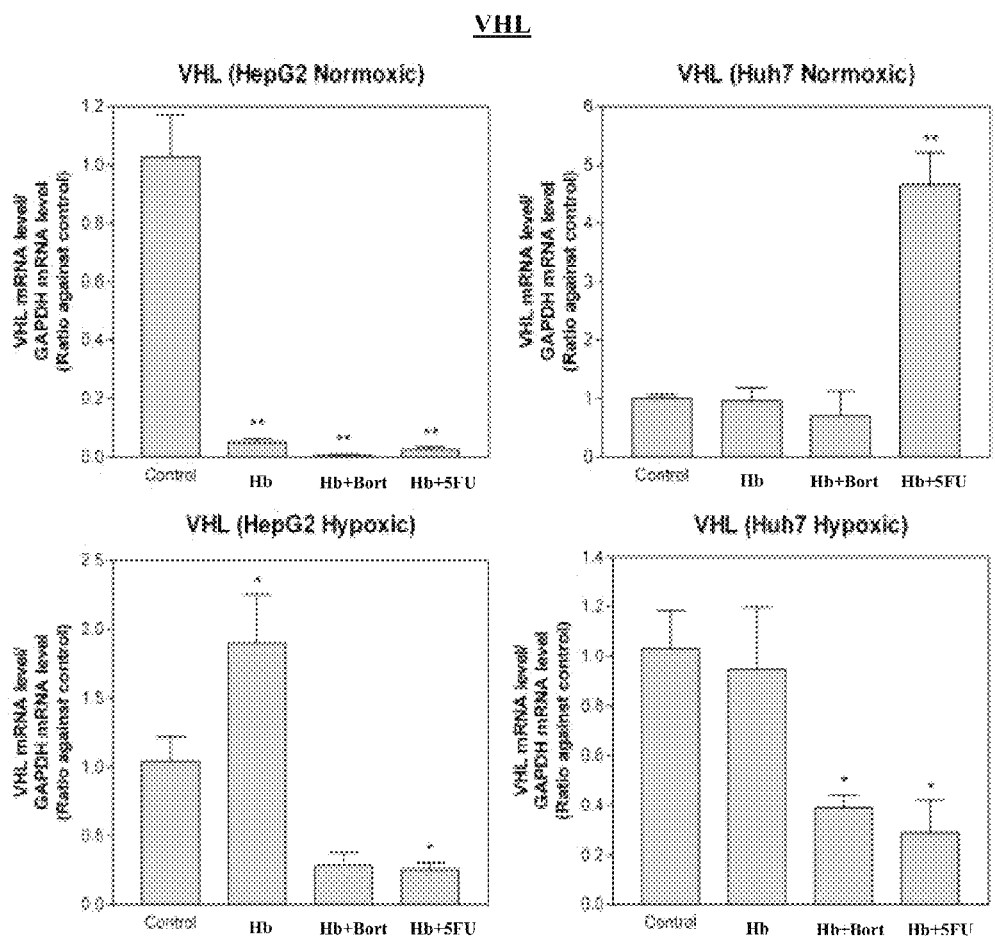
FIG. 8 shows the expression of von Hippel-Lindau (VHL) gene in liver cancer cells (HepG2 and Huh7) after treating with different concentrations of heat stable hemoglobin-based oxygen carrier and under normoxic vs hypoxic conditions.
Figure 9:
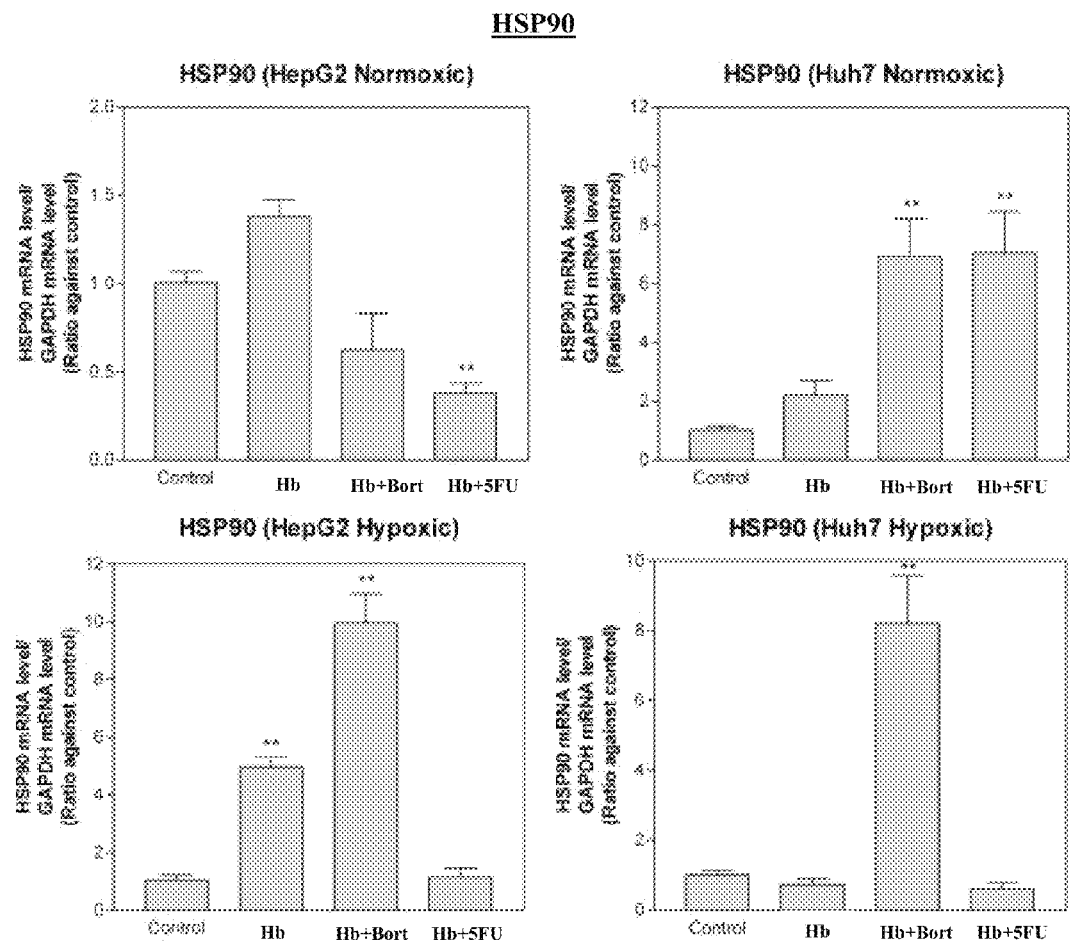
FIG. 9 shows the expression of a heat shock protein 90 (HSP90) gene in liver cancer cells after treating with different concentrations of heat stable hemoglobin-based oxygen carrier and under normoxic vs hypoxic conditions.

In FIG. 3, Hb is demonstrated to affect HIF1 α protein expression in the HepG2 and the metastatic Huh7 liver cancer models. Hb downregulates HIF1 α in both normoxia and hypoxia, suggesting that the depletion of HIF1 α by Hb alone (40% compared with untreated control) affects the binding of HIF1 α to its downstream effectors and results in transcriptional repression of these effector genes. Similar downregulation patterns can be detected in the upstream regulators of HIF1 α (FIG. 4), heat shock protein 90 (HSP90) (FIG. 9) and von Hippel-Lindau (VHL) (FIG. 8), after treatment with Hb.

Figure 5:
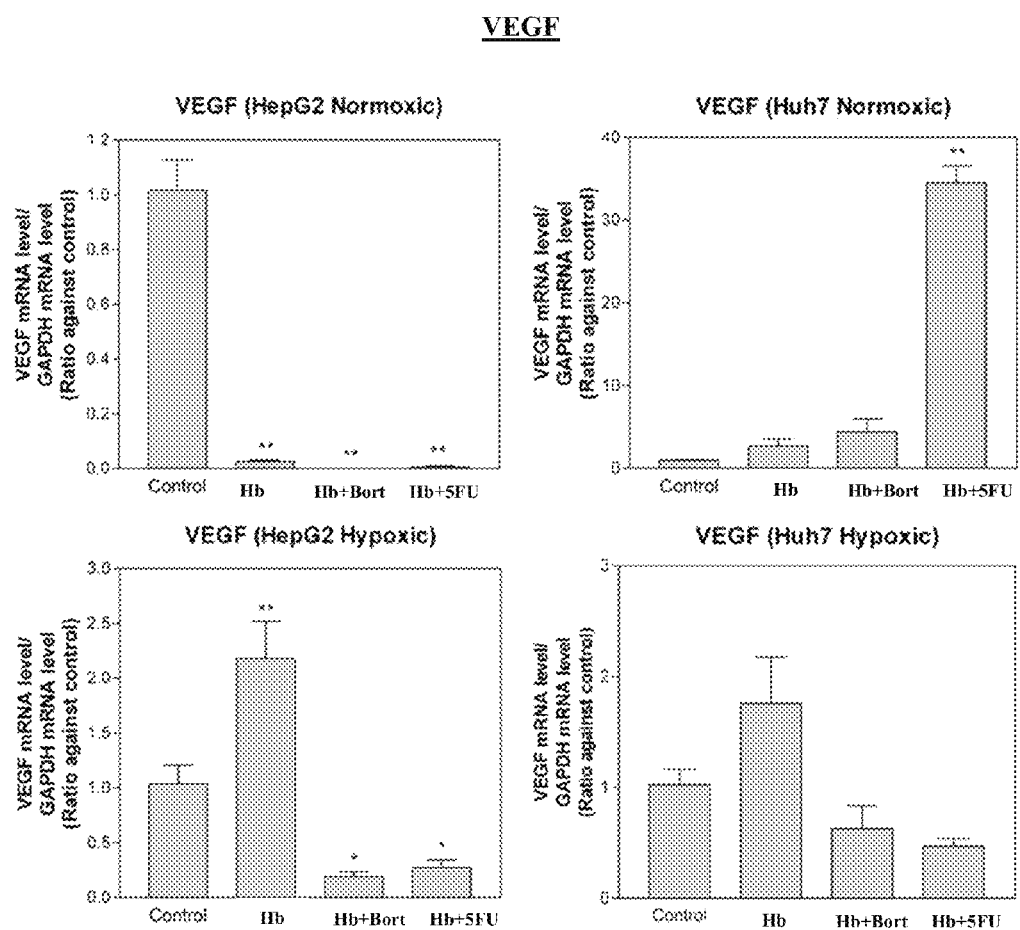
FIG. 5 shows the expression of Vascular Endothelial Growth Factor (VEGF) gene in liver cancer cells (HepG2 and Huh7) after treating with different concentrations of heat stable hemoglobin-based oxygen carrier and under normoxic vs hypoxic conditions.
Figure 6:
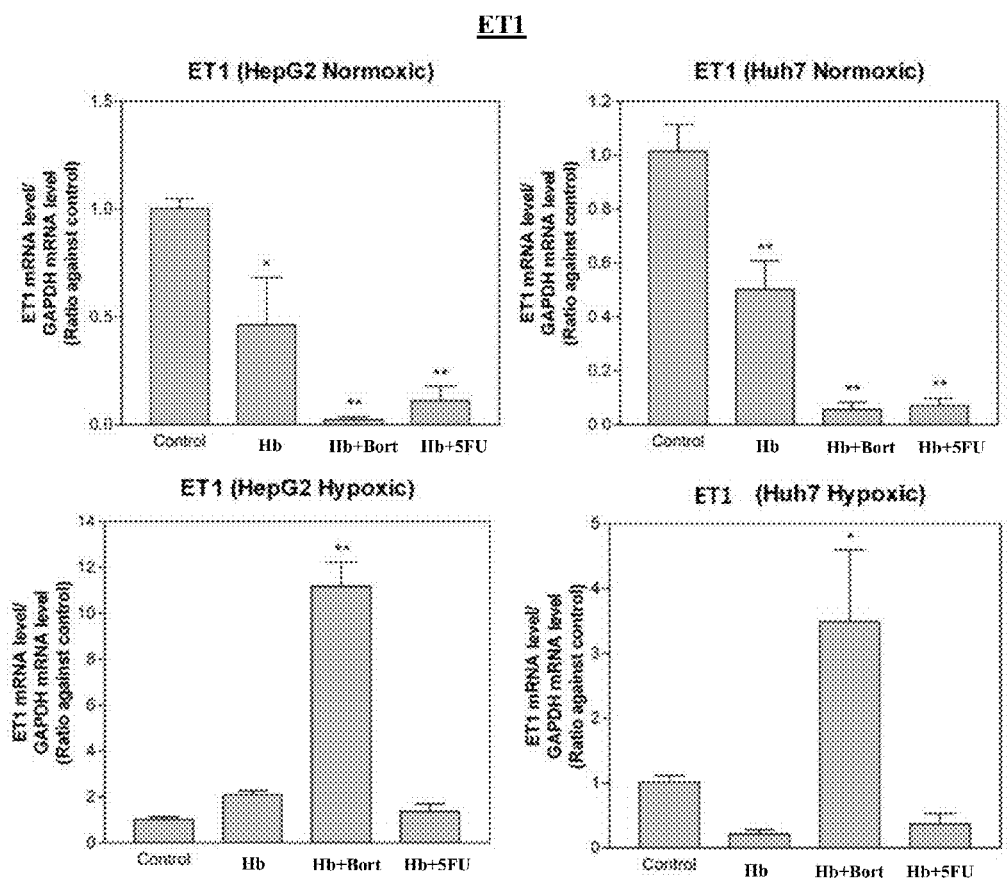
FIG. 6 shows the expression of endothelin-1 (ET1) gene in liver cancer cells (HepG2 and Huh7) after treating with different concentrations of heat stable hemoglobin-based oxygen carrier and under normoxic vs hypoxic conditions.
Figure 7:
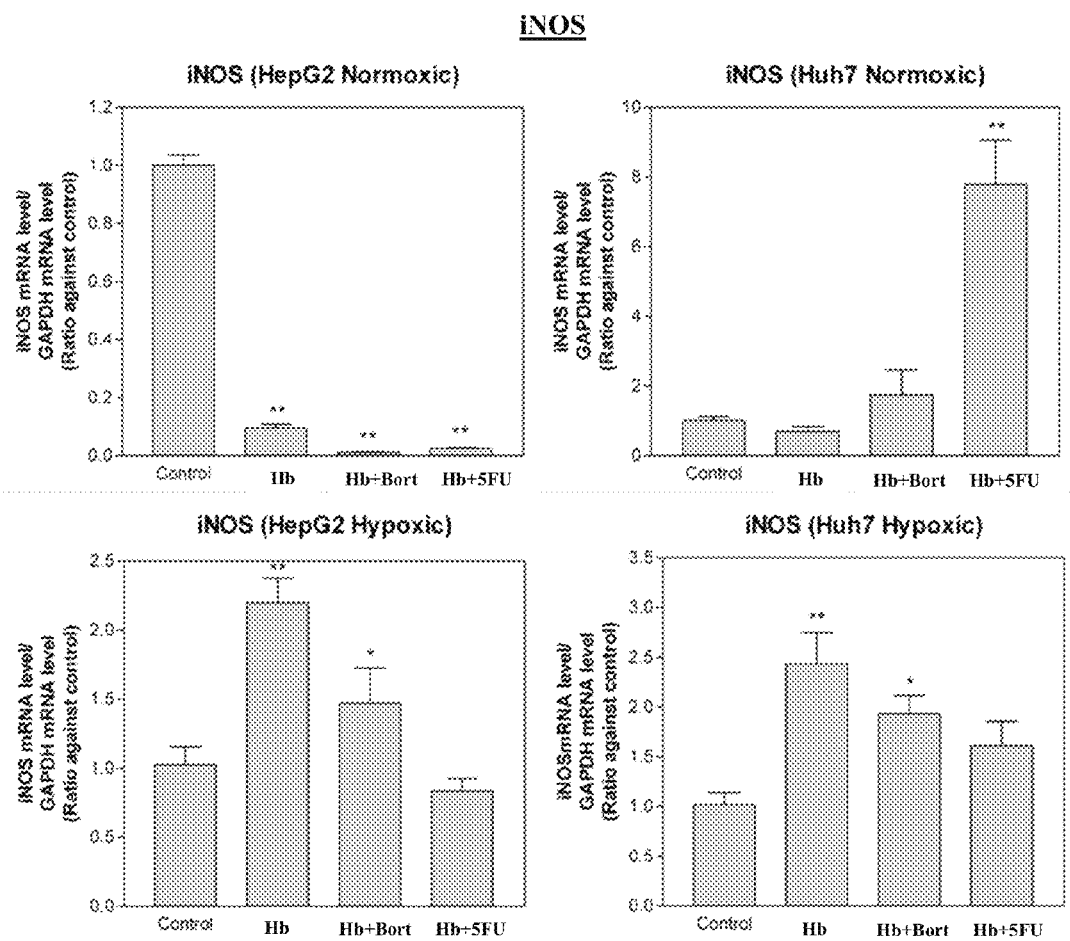
FIG. 7 shows the expression of inducible nitric oxide synthase (iNOS) gene in liver cancer cells (HepG2 and Huh7) after treating with different concentrations of heat stable hemoglobin-based oxygen carrier and under normoxic vs hypoxic conditions.
Figure 10:
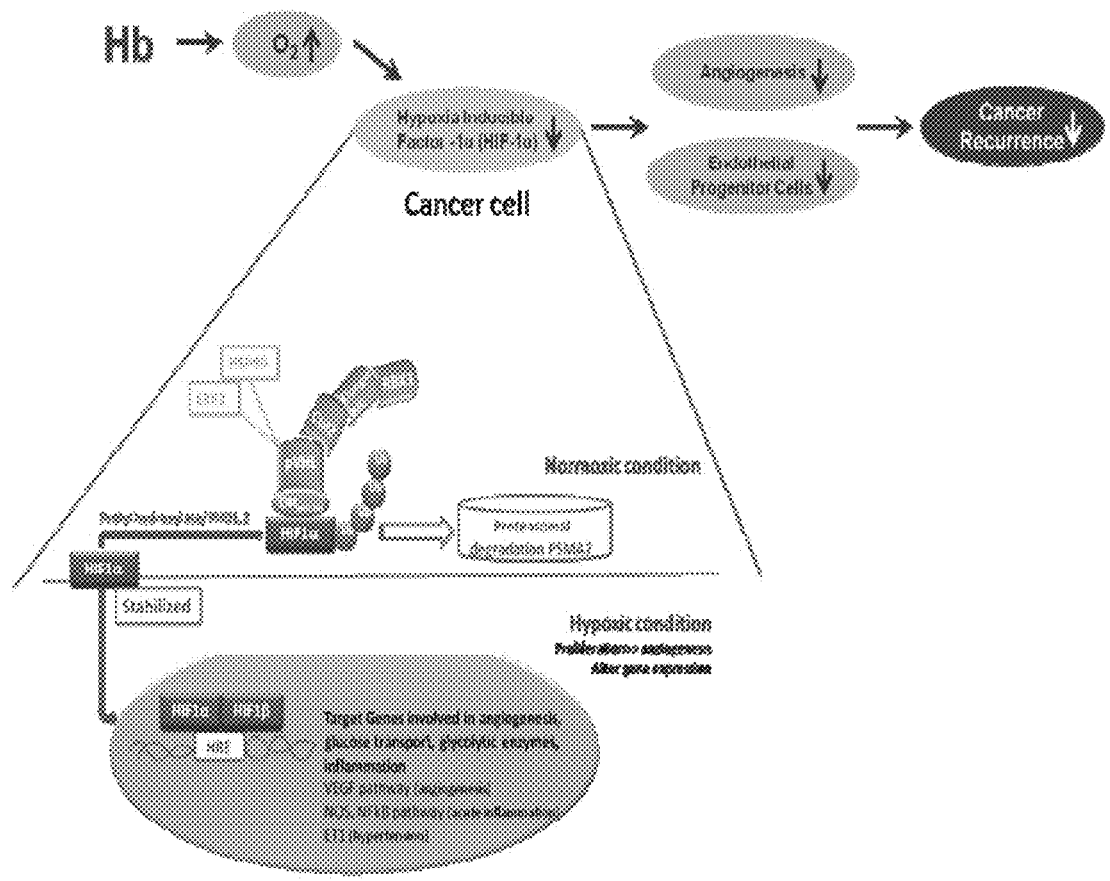
FIG. 10 is a schematic diagram illustrating the proposed mechanism and signaling cascade involved in the inhibitory effect of the heat stable hemoglobin-based oxygen carrier on tumor recurrence.

A substantial reduction of HIF1 α is detected, both transcript and protein levels exemplified by respective quantitative qPCR and Western blotting studies, when liver cancer cells are treated with Hb and 5FU (95% suppression) or Hb and Bortezomib (80% suppression). These data suggests that Hb alone, Hb combined treatment with 5FU or Bortezomib can abolish the hypoxia-induced HIF1 α mRNA and protein stabilization. As a consequence, the downregulation of vascular endothelial growth factor (VEGF) (FIG. 5) and endothelin-1 (ET1) (FIG. 6) expression in Huh7 cells are observed, suggesting that the combination of Hb and 5FU or Hb and Bortezomib can inhibit angiogenesis and vascular tone in the liver metastatic model, where the inhibition of angiogenesis is intrinsically connected to the development of metastasis. The combination treatments are observed to reduce inducible nitric oxide synthase (iNOS) (FIG. 7) expression in Huh7, suggesting that the degree of vasculature and angiogenesis can also be compromised in the liver metastatic model. In total, our findings indicate that combined administration of Hb with 5FU or Bortezomib can synergistically repress hypoxic induction of VEGF, ET1 and iNOS expressions by inhibiting HIF1 α. The proposed mechanism involved in the inhibitory effect of Hb on tumor recurrence and its signaling cascade is illustrated in FIG. 10. The relationship of oxygen supply, prolyl hydroxylase domain-containing protein (PDH), HIF and endothelial progenitor cell (EPC) is clearly shown.

Figure 11:
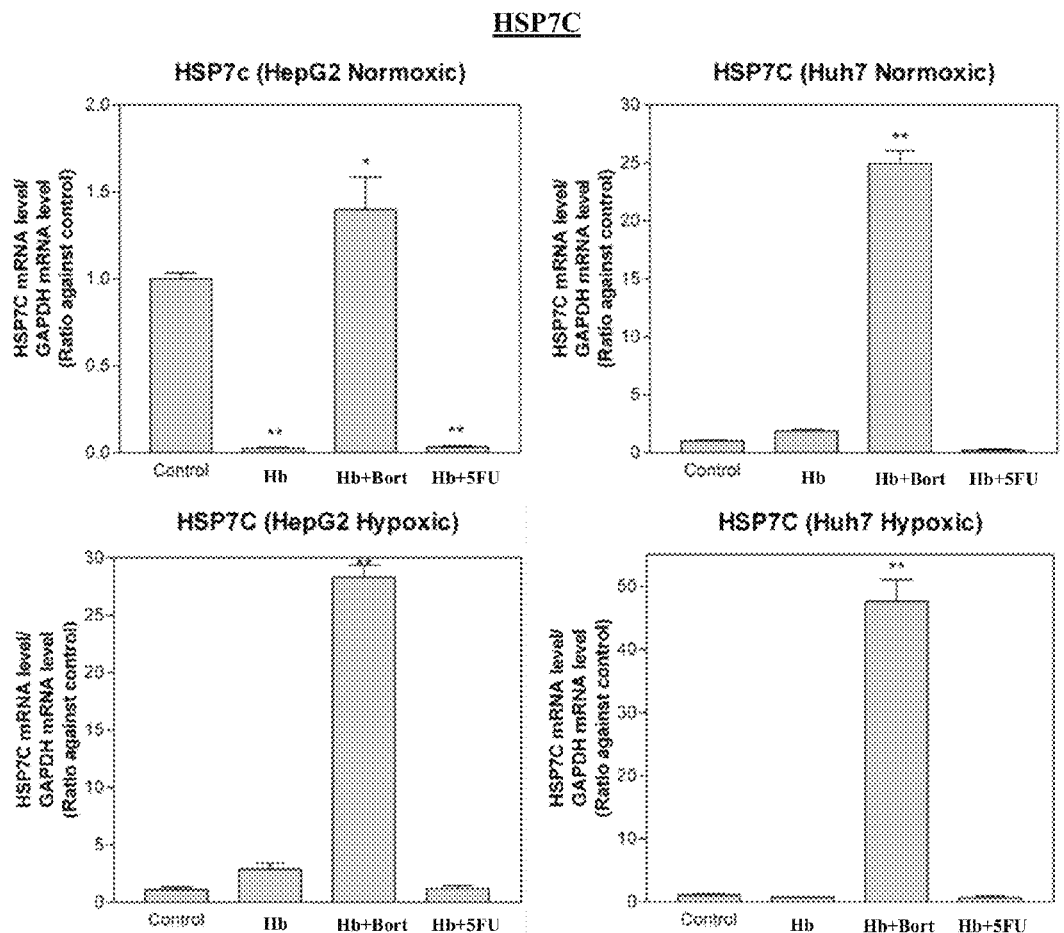
FIG. 11 shows the expression of the heat shock protein 7C (HSP7C) gene in liver cancer cells after treating with different concentrations of heat stable hemoglobin-based oxygen carrier and under normoxic vs hypoxic conditions.
Figure 12:
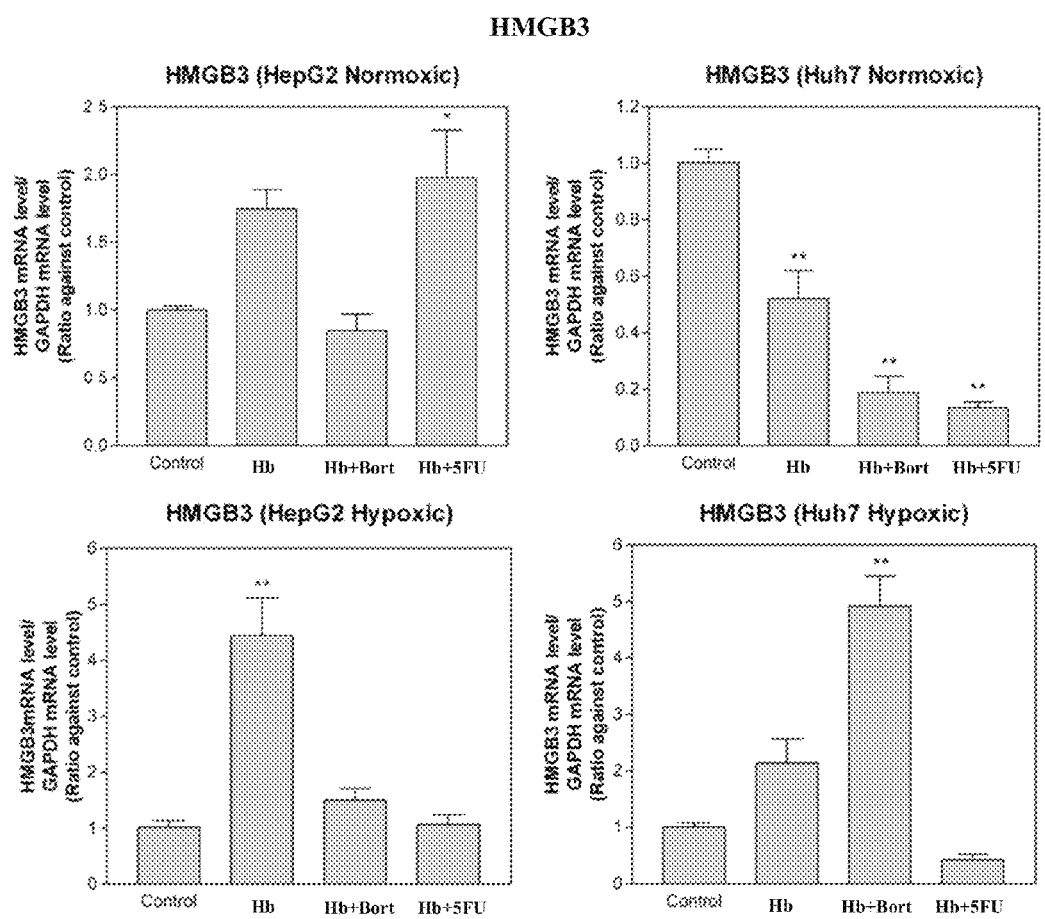
FIG. 12 shows the expression of high-mobility group box 3 (HMGB3) gene in liver cancer cells after treating with different concentrations of heat stable hemoglobin-based oxygen carrier and under normoxic vs hypoxic conditions.
Figure 13:
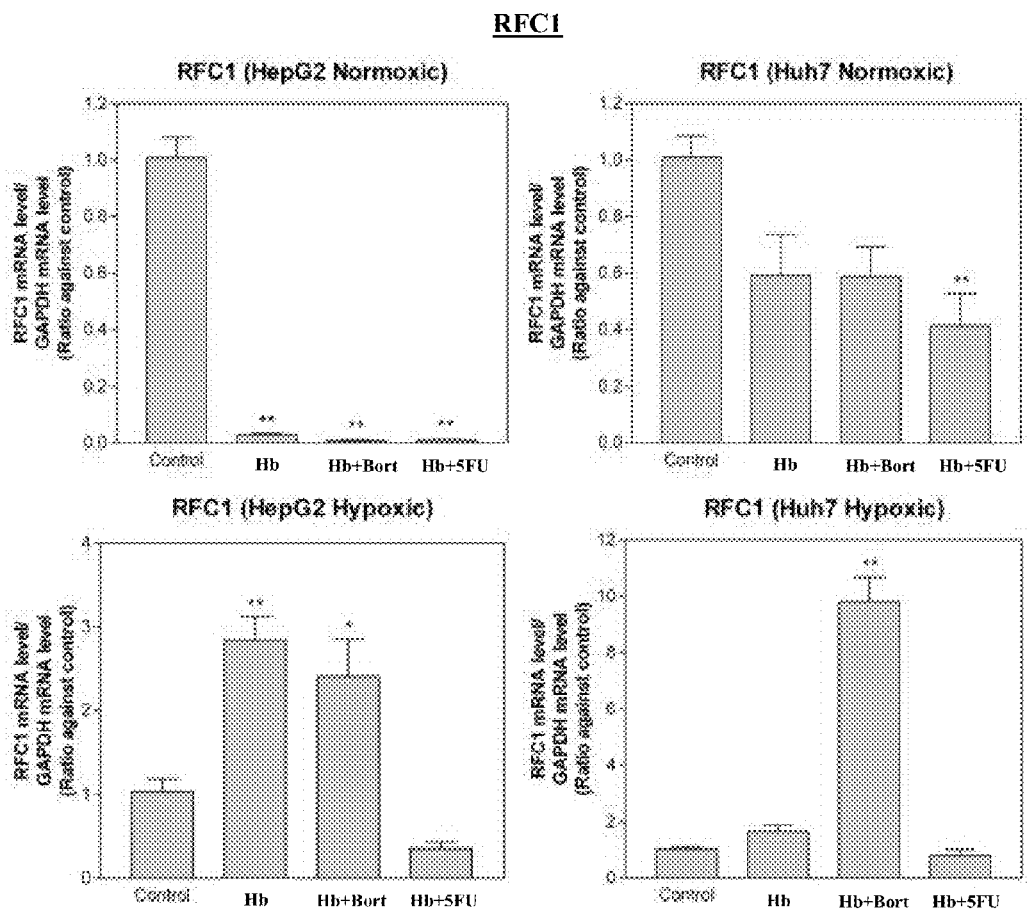
FIG. 13 shows the expression of replication factor 1C (RFC1) gene in liver cancer cells after treating with different concentrations of heat stable hemoglobin-based oxygen carrier and under normoxic vs hypoxic conditions.

A pharmaceutical composition including a hemoglobin-based oxygen carrier configured to target DNA-damage-sensing cell regulation apparatus is also found to go through novel regulatory pathways. In the present invention, two of the proteins which are the intrinsic parts of the DNA-damage-sensing apparatus, replication factor 1C (RFC1) (FIG. 13) and the HSP7C (heat shock protein 7C) (FIG. 11), are upregulated in Hb-treated liver cancer cells, and are drastically upregulated in the combined treatment with Bortezomib (3-10 fold upregulation for RFC1, and 25-45 fold upregulation for HSP7C). These novel Hb target proteins suggest that Hb is a potential Reactive Oxygen Species (ROS) inducer, and it is clearly important for the metastatic liver cancer cells, Huh7, to sense and respond to the ROS-mediated DNA damage. The drastic upregulation of the DNA damage response proteins in reaction with Hb and Bortezomib may result in subsequent oxidative-stress induced apoptosis.

For uses in cancer treatment, the oxygen carrier-containing pharmaceutical composition of the present invention serves as a tissue oxygenation agent to improve the oxygenation in tumor tissues, thereby enhancing chemosensitivity and radiation sensitivity.

In addition, the ability of the heat stable tetrameric hemoglobin to improve oxygenation in normal tissues (FIG. 14) and in extremely hypoxic tumors (FIG. 15), is demonstrated in this invention. Oxygen partial pressure ($pO_2$) within the tumor mass is directly monitored by a fibreoptic oxygen sensor (Oxford Optronix Limited) coupled with a micro-positioning system (DTI Limited). After intravenous injection of 0.2 g/kg of the heat stable tetrameric hemoglobin, the median $pO_2$ value rises from baseline to about two-fold of relative mean oxygen partial pressure within 15 minutes and extends to 6 hours. Further, the oxygen level on average still maintains a level of 25% to 30% above the baseline value 24 to 48 hours post infusion. No commercial products or existing technologies show as high an efficacy when compared to the oxygen carrier-containing pharmaceutical composition prepared in this invention.

Figure 15:
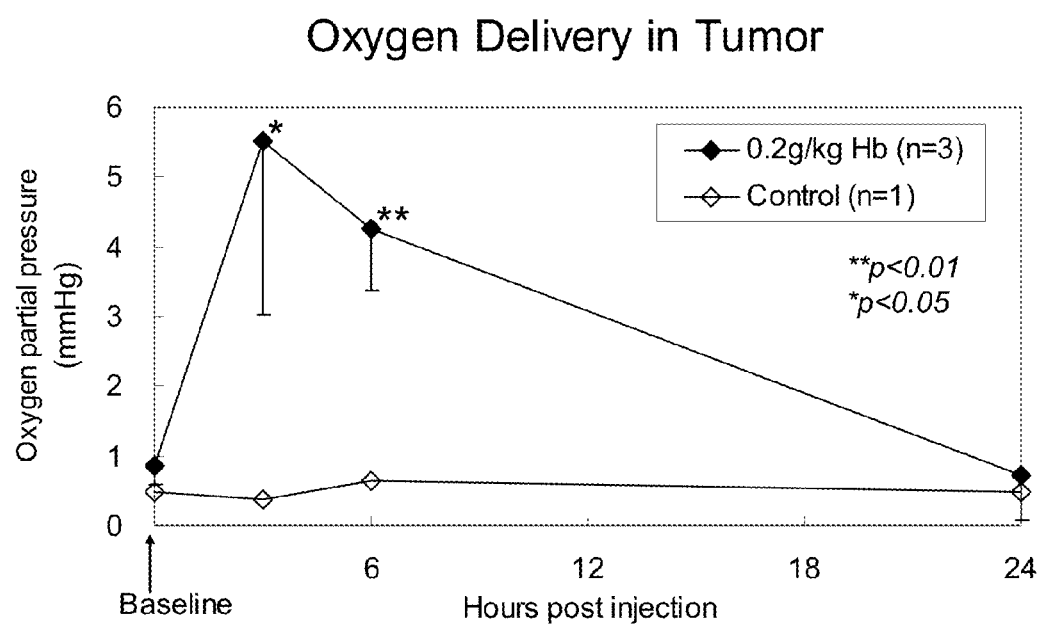
FIG. 15 shows an improvement of oxygenation in hypoxic tumor tissue. Injection of 0.2 g/kg heat stable tetrameric hemoglobin solution results in a significant increase in oxygen delivery to the head and neck squamous cell carcinoma (HNSCC) xenograft.

For tumor tissue oxygenation, a representative oxygen profile of a human head and neck squamous cell carcinoma (HNSCC) xenograft (FaDu) is shown in FIG. 15. After intravenous injection of 0.2 g/kg of the heat stable tetrameric hemoglobin, a significant increase in the mean $pO_2$ of more than 6.5-fold and 5-fold is observed at 3 and 6 hours, respectively (FIG. 15).

Figure 16:
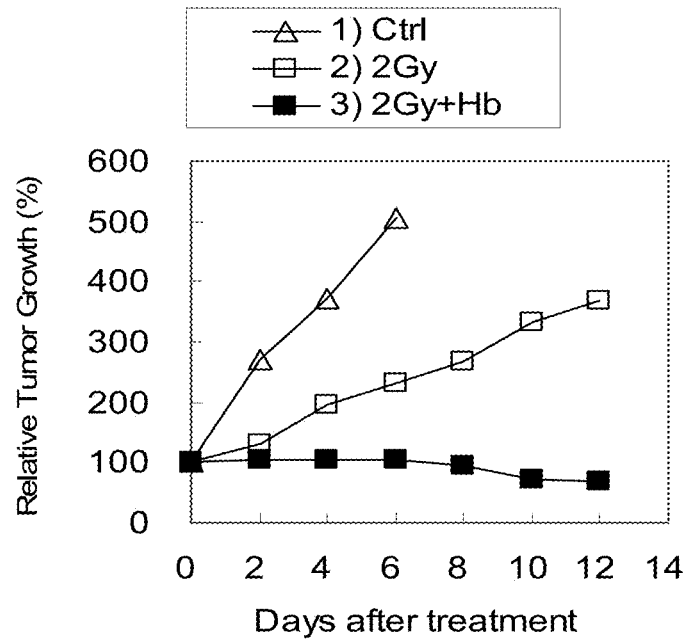
FIG. 16 shows partial tumor shrinkage in rodent models of (A) nasopharyngeal carcinoma (NPC) and (B) liver tumor.
Figure 16:
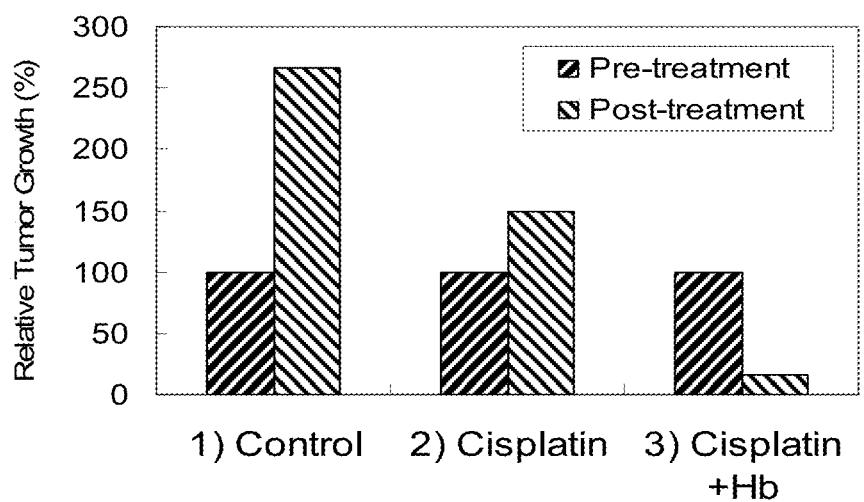

For applications in cancer treatment, the oxygen carrier-containing pharmaceutical composition of the present invention serves as a tissue oxygenation agent to improve the oxygenation in tumor tissues, thereby enhancing chemo- and radiation sensitivity. In conjunction with X-ray irradiation and the heat stable tetrameric hemoglobin, tumor growth is delayed. In FIG. 16A, the representative curves show significant tumor shrinkage in rodent models of nasopharyngeal carcinoma. Nude mice bearing CNE2 xenografts are treated with X-ray alone (2Gy) or in combination with the heat stable tetrameric hemoglobin (2Gy+Hb). 1.2 g/kg of the heat stable tetrameric hemoglobin is injected intravenously into the mouse approximately 3 to 6 hours before X-ray irradiation and results in a partial shrinkage of nasopharyngeal carcinoma xenograft.

In one embodiment, significant liver tumor shrinkage is observed after injecting the composition, in conjunction with a chemotherapeutic agent. In FIG. 16B, the representative chart shows significant tumor shrinkage in a rat orthotopic liver cancer model. Buffalo rats bearing a liver tumor orthograft (CRL1601 cell line) are treated with 3 mg/kg cisplatin alone, or in combination with 0.4 g/kg of the heat stable tetrameric hemoglobin (Cisplatin+Hb). Administration of the heat stable tetrameric hemoglobin before cisplatin injection results in a partial shrinkage of the liver tumor.

EXAMPLES

The following examples are provided by way of describing specific embodiments of this invention without intending to limit the scope of this invention in any way.

Example 1

Culture and Reagents for Liver Cancer Cell Line

HepG2 and Huh7 cell lines are used. These cells are cultured in DMEM (Invitrogen) with 10% Fetal bovine serum (FBS), 100 U/ml penicillin and 100 μg/ml streptomycin at 37° C. For normoxic condition, cells are incubated with ambient $O_2$ concentration and 5% $CO_2$; for hypoxic condition, cells are incubated with 0.1-0.5% $O_2$ (Quorum FC-7 automatic $CO_2/O_2/N_2$ gas mixer) and 5% $CO_2$.

Example 2

Live Cell Time-Lapse Microscopy

HepG2 or Huh7 cells are seeded onto glass bottom microwell dishes (MatTek Corporation). Live cells at defined zooms (63×, 20×) are acquired using Zeiss Observer.Z1 widefield microscope, equipped with atmospheric/temperature-controlled chamber and motorized stage for multi-positional acquisition. The incubation is performed in an enclosed live cell imaging system purged with 0.1% $O_2$ and 5% $CO_2$ (premixed). Cells transfected with pcDNA3, pRFP-Caveolin1, or pRFP-Clathrin are exposed to HB-FITC for 15 min prior to the acquisition of images every 3 min for a period of 2 hours. Images are deconvolved and compacted into time-lapse movies using the MetaMorph software (Molecular Device).

Example 3

Cytotoxicity Assay

Cell viability is measured using a 3-(4,5-dimethylthiazol-2-yl)-2,5-diphenyltetrazolium bromide (MTT) proliferation assay. Briefly, HepG2 or Huh7 cells are seeded in a 96-well flat-bottomed microplate (6000 cells/well) and cultured in 100 μL growth medium at 37° C. and 5% $CO_2$ for 24 h. Cell culture medium in each well is then replaced by 100 μL cell growth medium, containing either no drug, Hb alone or Hb with another chemotherapeutics at their $IC_{50}$ concentrations. Incubation of Hb for 24 h, 20 μL MTT labeling reagent (5 mg/mL in PBS solution) is added to each well for further 4 h at 37° C. The growth medium is removed gently, and 200 μL DMSO is then added to each well as solubilizing agent to dissolve the formazan crystals completely. The absorbance at the wavelength of 570 nm is measured by Multiskan EX (Thermo Electron Corporation), and each data point represents the means±SD from triplicate wells.

Example 4

RNA Isolation and Quantitative Real-Time PCR

Total RNA is isolated using the Trizol reagent (Invitrogen) and 5 μg of the total RNA is reverse transcribed with an oligo-dT primer and Superscript II reverse transcriptase (Invitrogen). One-tenth of the first strand cDNA is used for quantitative measurements of HIF1alpha, VHL, HSP90, VEGF, iNOS, ET1, HSP7c, RFC1, HMGB3, and GAPDH transcript levels by the SYBR Green PCR Master Mix kit (Applied Biosystems) with specific primers (shown below). The fluorescence signals are measured in real time during the extension step by the 7900HT Fast Real Time PCR System (Applied Biosystems). The threshold cycle (Ct) is defined as the fractional cycle number at which the fluorescence signal reached 10-fold standard deviation of the baseline (from cycles 2 to 10). The ratio change in the target gene relative to the GAPDH control gene is determined by the $2^{-\Delta\Delta Ct}$ method.

```
HIF1α:
SEQ NO. 1: Forward Primer:
5-GGCGCGAACGACAAGAAAAAG-3 (420-440)

SEQ NO. 2: Reverse Primer:
5-CCTTATCAAGATGCGAACTCACA-3 (21-44)

SEQ NO. 3: Forward Primer:
CAGAGCAGGAAAAGGAGTCA (2414-2433)

SEQ NO. 4: Reverse Primer:
AGTAGCTGCATGATCGTCTG (2645-2625)

SEQ NO. 5: Forward Primer:
5'-AATGGAATGGAGCAAAAGACAATT-3' (2694-2720)

SEQ NO. 6: Reverse Primer:
5'-ATTGATTGCCCCAGCAGTCTAC-3' (2764-2743)

VEGF:
SEQ NO. 7: Forward Primer:
GCTACTGCCATCCAATCGAG (1187-1206)

SEQ NO. 8: Reverse Primer:
CTCTCCTATGTGCTGGCCTT (1395-1376)

SEQ NO. 9: Forward Primer:
5'-CTCTCTCCCTCATCGGTGACA-3' (3146-3167)

SEQ NO. 10: Reverse Primer:
5'-GGAGGGCAGAGCTGAGTGTTAG-3' (3202-3223)

SEQ NO. 11: Forward Primer:
ACTGCCATCCAATCGAGACC (1190-1209)

SEQ NO. 12: Reverse Primer:
GATGGCTGAAGATGTACTCGATCT (1265-1241)

INOS:
SEQ NO. 13: Forward Primer:
5'-ACAACAAATTCAGGTACGCTGTG-3' (2111-2137)

SEQ NO. 14: Reverse Primer:
5'-TCTGATCAATGTCATGAGCAAAGG-3' (2194-2171)

SEQ NO. 15: Forward Primer:
GTTCTCAAGGCACAGGTCTC (121-140)

SEQ NO. 16: Reverse Primer:
GCAGGTCACTTATGTCACTTATC (225-247)

ET1:
SEQ NO. 17: Forward Primer:
TGCCAAGCAGGAAAAGAACT (701-720)
```

-continued

SEQ NO. 18: Reverse Primer:
TTTGACGCTGTTTCTCATGG (895-876)

HSP90:
SEQ NO. 19: Forward Primer:
TTCAGACAGAGCCAAGGTGC (640-659)

SEQ NO. 20: Reverse Primer:
CAATGACATCAACTGGGCAAT (807-787)

SEQ NO. 21: Forward Primer:
GGCAGTCAAGCACTTTTCTGTAG (1032-1054)

SEQ NO. 22: Reverse Primer:
GTCAACCACACCACGGATAAA (1230-1210)

VHL:
SEQ NO. 23: Forward Primer:
ATTAGCATGGCGGCACACAT (2806-2825)

SEQ NO. 24: Reverse Primer:
TGGAGTGCAGTGGCATACTCAT (2921-2900)

Example 5

Western Blotting Analysis

Cells are harvested and protein concentrations are determined. Protein (30 μg) is resolved on 10% SDS-PAGE, transferred onto a nitrocellulose membrane (PVDF, BioRad). Actin is used as loading control. Relative protein expression levels are quantified by gel documentation system (Ultra-Violet Product Ltd).

Example 6

Improvement of Oxygenation (6a) Improvement of Oxygenation in Normal Tissue

Figure 14:
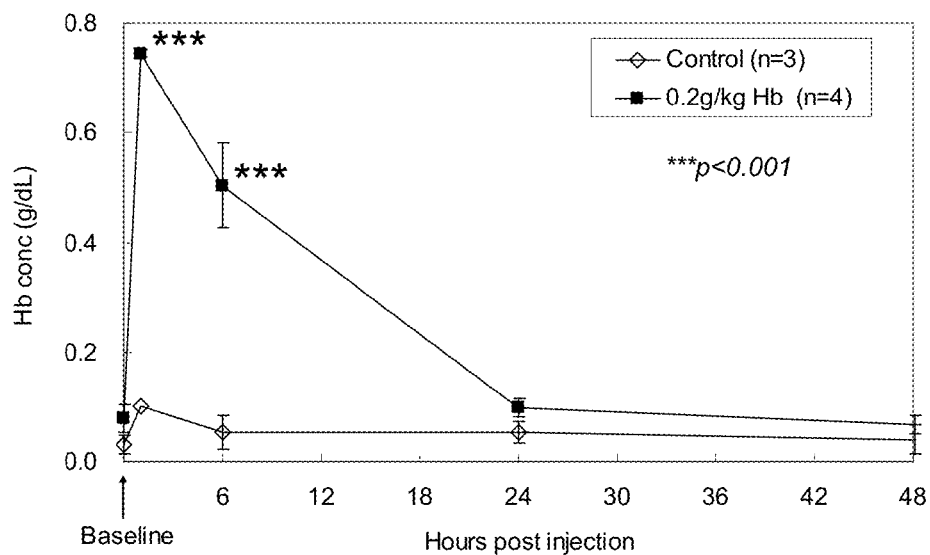
FIG. 14 shows an improvement of oxygenation in normal tissue. Injection of 0.2 g/kg heat stable tetrameric hemoglobin solution results in a significant increase in (A) plasma hemoglobin concentration and (B) oxygen delivery to muscle.
Figure 14:
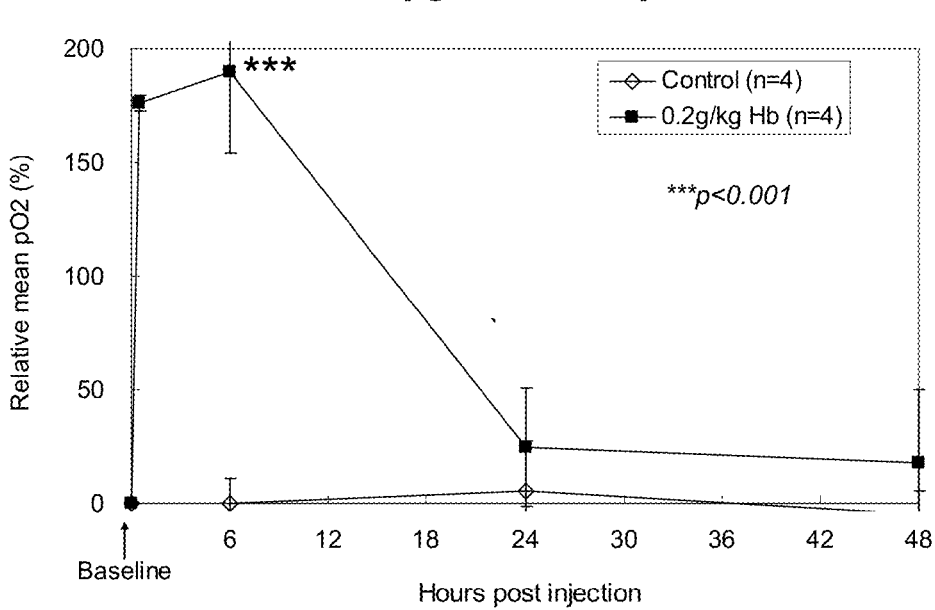

Some studies for the normal tissue oxygenation by heat stable tetrameric hemoglobin are carried out (shown in FIG. 14). A comparative pharmacokinetic and pharmacodynamic study is conducted in buffalo rats. Male inbred buffalo rats are individually administered with 0.2 g/kg heat stable tetrameric hemoglobin solution or ringer's acetate buffer (control group). The concentration-time profile of plasma hemoglobin is determined by Hemocue™ photometer at 1, 6, 24, 48 hours and compared with the baseline reading. The methods are based on photometric measurement of hemoglobin where the concentration of hemoglobin is directly read out as g/dL. Oxygen partial pressure ($pO_2$) is directly measured by the Oxylab™ tissue oxygenation and temperature monitor (Oxford Optronix Limited) in hind leg muscle of buffalo rats. Rats are anesthetized by intra-peritoneal injection of 30-50 mg/kg pentobarbitone solution followed by insertion of oxygen sensor into the muscle. All $pO_2$ readings are recorded by Datatrax2 data acquisition system (World Precision Instrument) in a real-time manner. Results demonstrate that after an intravenous injection of 0.2 g/kg of the heat stable tetrameric hemoglobin, the mean $pO_2$ value rises from baseline to about two-fold of the relative mean oxygen partial pressure within 15 minutes and extends to 6 hours. Further, the oxygen level on average is still maintained at 25% to 30% above the baseline value 24 to 48 hours post injection (FIG. 14B).

(6b) Significant Improvement of Oxygenation in Extremely Hypoxic Tumor Area

Improvement of oxygenation in an extremely hypoxic tumor area is evaluated by a human head and neck squamous cell carcinoma (HNSCC) xenograft model. A hypopharyngeal squamous cell carcinoma (FaDu cell line) is obtained from the American Type Culture Collection. Approximately $1 \times 10^6$ cancer cells are injected subcutaneously into four to six week-old inbred BALB/c AnN-nu (nude) mice. When the tumor xenograft reaches a diameter of 8-10 mm, oxygen partial pressure ($pO_2$) within the tumor mass is directly monitored by the Oxylab™ tissue oxygenation and temperature monitor (Oxford Optronix Limited). All $pO_2$ readings are recorded by the Datatrax2 data acquisition system (World Precision Instrument) in a real-time manner. When the $pO_2$ reading is stabilized, 0.2 g/kg heat stable tetrameric hemoglobin solution is injected intravenously through the tail vein of the mice and the tissue oxygenation is measured. Results demonstrate that after intravenous injection of 0.2 g/kg of the said heat stable tetrameric hemoglobin, a significant increase in the mean $pO_2$ of more than 6.5-fold and 5-fold is observed in 3 and 6 hours, respectively (FIG. 15).

Example 7

Cancer Treatment Studies: A Significant Tumor Shrinkage in Nasopharyngeal Carcinoma A significant tumor shrinkage is observed after administration of heat stable tetrameric hemoglobin solution in combination with X-ray irradiation (FIG. 16A). A human nasopharyngeal carcinoma xenograft model is employed. Approximately $1 \times 10^6$ cancer cells (CNE2 cell line) are injected subcutaneously into four to six week-old inbred BALB/c AnN-nu (nude) mice. When the tumor xenograft reaches a diameter of 8-10 mm, tumor-bearing mice are randomized into three groups as follows:

Group 1: Ringer's acetate buffer (Ctrl)
Group 2: Ringer's acetate buffer+X-ray irradiation (2Gy)
Group 3: Heat stable tetrameric hemoglobin+X-ray irradiation (2Gy+Hb)

Nude mice bearing CNE2 xenografts are irradiated with X-irradiation alone (Group 2) or in combination with heat stable tetrameric hemoglobin (Group 3). For X-ray irradiation (Groups 2 and 3), mice are anesthetized by an intra-peritoneal injection of 50 mg/kg pentobarbitone solution. 2 Grays of X-ray is delivered to the xenograft of tumor-bearing mice by a linear accelerator system (Varian Medical Systems). For Group 3, 1.2 g/kg heat stable tetrameric hemoglobin is injected intravenously through the tail vein into the mouse before X-ray treatment. Tumor dimensions and body weights are recorded every alternate day starting with the first day of treatment. Tumor weights are calculated using the equation $\frac{1}{2} \times LW^2$, where L and W represent the length and width of the tumor mass, measured by a digital caliper (Mitutoyo Co, Tokyo, Japan) at each measurement. Group 1 is the non-treatment control group. Results (shown in FIG. 16) demonstrate that significant shrinkage of the CNE2 xenograft is observed in mice treated with the heat stable tetrameric hemoglobin solution in conjunction with X-irradiation (Group 3, FIG. 16A).

Example 8

Cancer Treatment Studies: A Significant Shrinkage in Liver Tumor

In addition, significant tumor shrinkage is observed after administration of heat stable tetrameric hemoglobin solution in combination with cisplatin (FIG. 16B). A rat orthotopic liver cancer model is employed. Approximately $2 \times 10^6$ rat liver tumor cells labeled with luciferase gene (CRL1601-Luc) are injected into the left lobe of the liver in a buffalo rat. Tumor growth is monitored by a Xenogen in vivo imaging system. Two to three weeks after injection, the tumor tissue is harvested, dissected into small pieces and orthotopically implanted into the left liver lobe of a second group of rats. Rats bearing liver tumor are randomized into three groups as follows:

Group 1: Ringer's acetate buffer (Control)
Group 2: Ringer's acetate buffer+cisplatin (Cisplatin)
Group 3: Heat stable tetrameric hemoglobin+cisplatin (Cisplatin+Hb)

Rats implanted with liver tumor tissue are treated with 3 mg/kg of cisplatin alone (Group 2) or in conjunction with heat stable tetrameric hemoglobin (Group 3). For groups 2 and 3, rats are anesthetized by an intra-peritoneal injection of 30-50 mg/kg pentobarbitone solution and cisplatin are administered via the left portal vein. For Group 3, 0.4 g/kg heat stable tetrameric hemoglobin is injected intravenously before cisplatin treatment. Group 1 is the non-treatment control group Importantly, a significant shrinkage of liver tumor is observed 3 weeks after treatment (FIG. 16B).

Example 9

Method of Preventing Post-Operative Liver Tumor Recurrence and Metastasis

Surgical resection of liver tumors is a frontline treatment of liver cancer. However, post-operative recurrence and metastasis of cancer remains a major attribute of unfavorable prognosis in these patients. For instance, previous studies reported that hepatic resection is associated with a 5-year survival rate of 50% but also a 70% recurrence rate. Follow-up studies on hepatocellular carcinoma (HCC) patients also reveal that extrahepatic metastases from primary HCC were detected in approximately 15% of HCC patients with the lungs being the most frequent site of extrahepatic metastases. It has been suggested that surgical stress, especially ischemia/reperfusion (IR) injury introduced during liver surgery is a major cause of tumor progression. Conventionally, hepatic vascular control is commonly used by surgeons to prevent massive hemorrhage during hepatectomy. For example, inflow occlusion by clamping of the portal triad (Pringle maneuver) has been used to minimize blood loss and reduce the requirement of perioperative transfusions. A recent Japanese study shows that 25% surgeons apply a Pringle maneuver on a routine basis. However, Pringle maneuver induces various degrees of ischemic injury in the remnant liver and is associated with cancer recurrence and metastasis.

Association of IR injury and tumor progression is also supported by previous animal studies. Firstly, the effect of IR injury and hepatic resection on liver cancer recurrence and metastasis was demonstrated in a recent study with an orthotopic liver cancer model. Hepatic IR injury and hepatectomy resulted in prominent recurrence and metastasis of liver tumors. Similar results were obtained in a colorectal liver metastasis mouse model where introduction of IR injury accelerates the outgrowth of colorectal liver metastasis.

Previously, several protective strategies have been studied for use to reduce IR injury during resection. For example, the application of a short period of ischemia before prolonged clamping, known as ischemic preconditioning (IP), was suggested to trigger hepatocellular defense mechanisms and has been used to reduce IR injury during liver resection. Others apply intermittent clamping (IC) procedures which allows cycles of inflow occlusion followed by reperfusion. Both methods were suggested to be effective in protecting against postoperative liver injury in non-cirrhotic patients undergoing major liver surgery. However, in a tumor setting, animal studies also show that IP failed to protect the liver against accelerated tumor growth induced by IR injury. In addition, some groups attempt to use anti-oxidants such as α-tocopherol and ascorbic acid to protect the liver from IR injury, thereby preventing liver metastasis. However, both anti-oxidants failed to restrict intrahepatic tumor growth stimulated by IR.

Mechanistically, different lines of evidence suggest hypoxia is associated with tumor recurrence and metastasis for a number of reasons: (1) studies show that hypoxic tumor is more resistant to radiation- and a chemo-therapy, tumor cells that survive the treatment are prone to recur; clinical evidence also suggests that patients with more hypoxic tumor areas have higher rates of metastases; (2) under hypoxic condition, cancer cells become more aggressive through the activation of hypoxia inducible factor-1 (HIF-1) pathway. This in turn triggers complementary responses involving pro-angiogenic factor vascular endothelial growth factor (VEGF) and receptors such as c-Met and CXCR4, which enhanced cell motility and homing to specific, distant organs; (3) recent studies also demonstrated that circulating cancer cells (CTCs) become more aggressive under hypoxic condition. Circulating tumor cells detected in the peripheral blood of cancer patients was shown to be an index of disease aggression in patients with distant metastasis, while hypoxia enabled those cells a more aggressive phenotype and diminished apoptotic potential. In particular, cancer stem cell population, which is more radio-resistant were enriched under reduced oxygen level in brain tumor.

Figure 17:
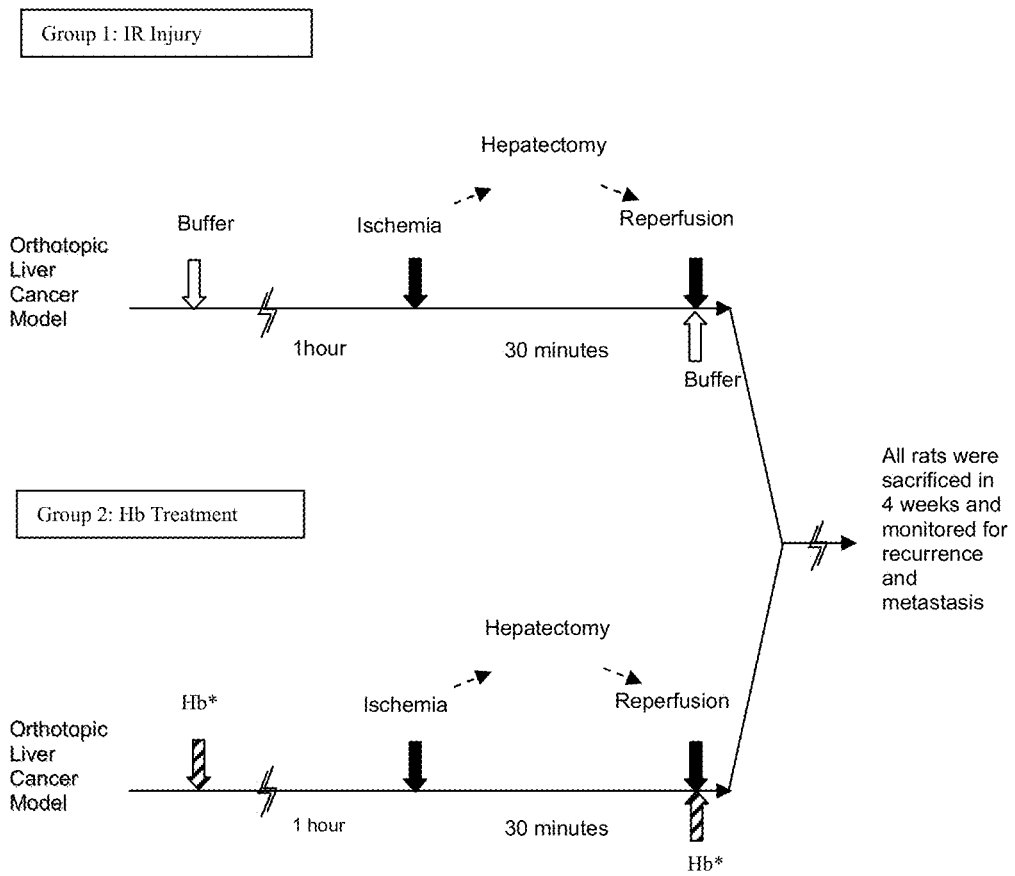
FIG. 17 shows a schematic drawing summarizing the surgical and hemoglobin product administration procedures during liver resection.

Therefore, in view of the above observations and studies, the cross-linked tetrameric hemoglobin of the present invention is used to prevent post-operative liver tumor recurrence and metastasis following hepatic resection. A rat orthotopic liver cancer model is established. Hepatocellular carcinoma cell line (McA-RH7777 cells) is used to establish the orthotopic liver cancer model in Buffalo rats (Male, 300-350 g). FIG. 17 shows a schematic drawing summarizing the surgical and hemoglobin product administration procedures. McA-RH7777 cells (approximately $1 \times 10^6$ cells/100 μL) are injected into the hepatic capsule of buffalo rat to induce solid tumor growth. Two weeks later (when the tumor volume reaches about 10×10 mm), tumor tissue is collected and cut into 1-2 mm$^3$ cubes and implanted into the left liver lobes of a new group of buffalo rats. Two weeks after orthotopic liver tumor implantation, the rats undergo liver resection (left lobe bearing liver tumor) and partial hepatic IR injury (30 minutes of ischemia on right lobe).

Two groups of rats with implanted tumor tissue are used for comparison of tumor recurrence and metastases. In group 1, rats are anesthetized with pentobarbital and administered intravenously with 0.2 g/kg at a concentration of 10 g/dL of the heat stable tetrameric hemoglobin of the present invention 1 hour before ischemia. Ischemia is introduced in the right lobe of the liver by clamping of right branches of hepatic portal vein and hepatic artery with a bulldog clamp. Subsequently, ligation is performed in the left liver lobe followed by resection of the left liver lobe bearing the liver tumor. At 30 minutes after ischemia, an additional 0.2 g/kg of the heat stable tetrameric hemoglobin is injected through the inferior vena cava followed by reperfusion. In group 2, ringer's acetate buffer is injected as a vehicle control with the same procedure. All rats are sacrificed 4 weeks after the hepatectomy procedures.

To examine tumor growth and metastasis, the liver and lungs of Buffalo rats are sampled at 4 weeks after Ischemia/reperfusion and hepatectomy procedures for morphological examination. Tissue is harvested, parafilm-embedded and sectioned followed by Hematoxylin and Eosin (H&E) staining. Local recurrence/metastasis (intrahepatic) and distant metastasis (lungs) are confirmed by histological examination.

Table 2 summarizes the comparison of tumor recurrence/metastasis at four weeks after liver resection and IR injury in a rat orthotopic liver cancer model.

TABLE 2

|  | Control (n = 13) | Treatment (n = 13) |
|---|---|---|
| Intrahepatic metastasis/recurrence | 9 (69.2%) | 4 (30.8%) |
| Lung metastasis | 7 (53.9%) | 4 (30.8%) |

To examine the protective effects of nonpolymeric heat stable tetrameric hemoglobin on liver tumor recurrence and metastasis, all rats are sacrificed 4 weeks after the hepatectomy and IR procedures. Lungs and liver tissues are harvested; hepatic tumor recurrence/metastasis and distant metastasis in the lungs are compared in both groups. Results show that the hemoglobin treatment decreases occurrence of recurrence and metastasis in both organs.

Figure 18:
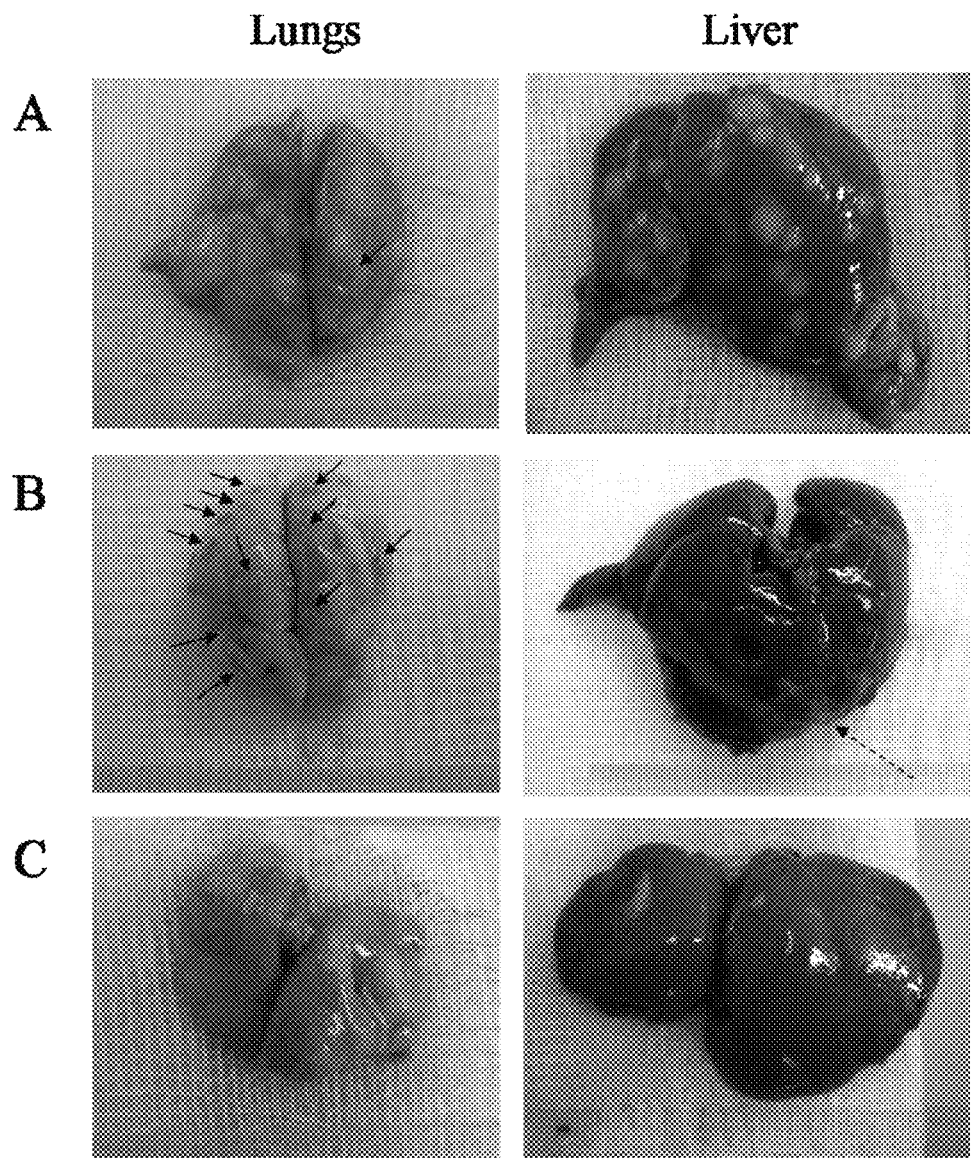
FIG. 18 shows representative examples of intra-hepatic liver cancer recurrence and metastasis and distant lung metastasis induced in the rats of the IR injury group after hepatectomy and ischemia/reperfusion procedures and its protection using the inventive heat stable tetrameric hemoglobin.

FIG. 18 shows representative examples of intra-hepatic liver cancer recurrence and metastasis and distant lung metastasis induced in the rats of the IR injury group after hepatectomy and ischemia/reperfusion procedures and its protection using the inventive heat stable tetrameric hemoglobin. In FIG. 18A, extensive intrahepatic liver cancer recurrence/metastasis is observed in the IR injury group. Distant lung metastasis is also occurred in the same rat (indicated by a solid arrow). In FIG. 18B, intrahepatic liver cancer recurrence/metastasis is observed in another case in the IR injury group (indicated by a dotted arrow). Extensive lung metastasis is observed in the same case (indicated by solid arrows). In contrast, FIG. 18C shows a representative example of protection from intrahepatic liver cancer recurrence/metastasis and distant lung metastasis in the inventive heat stable tetrameric hemoglobin treated rat.

Figure 19:
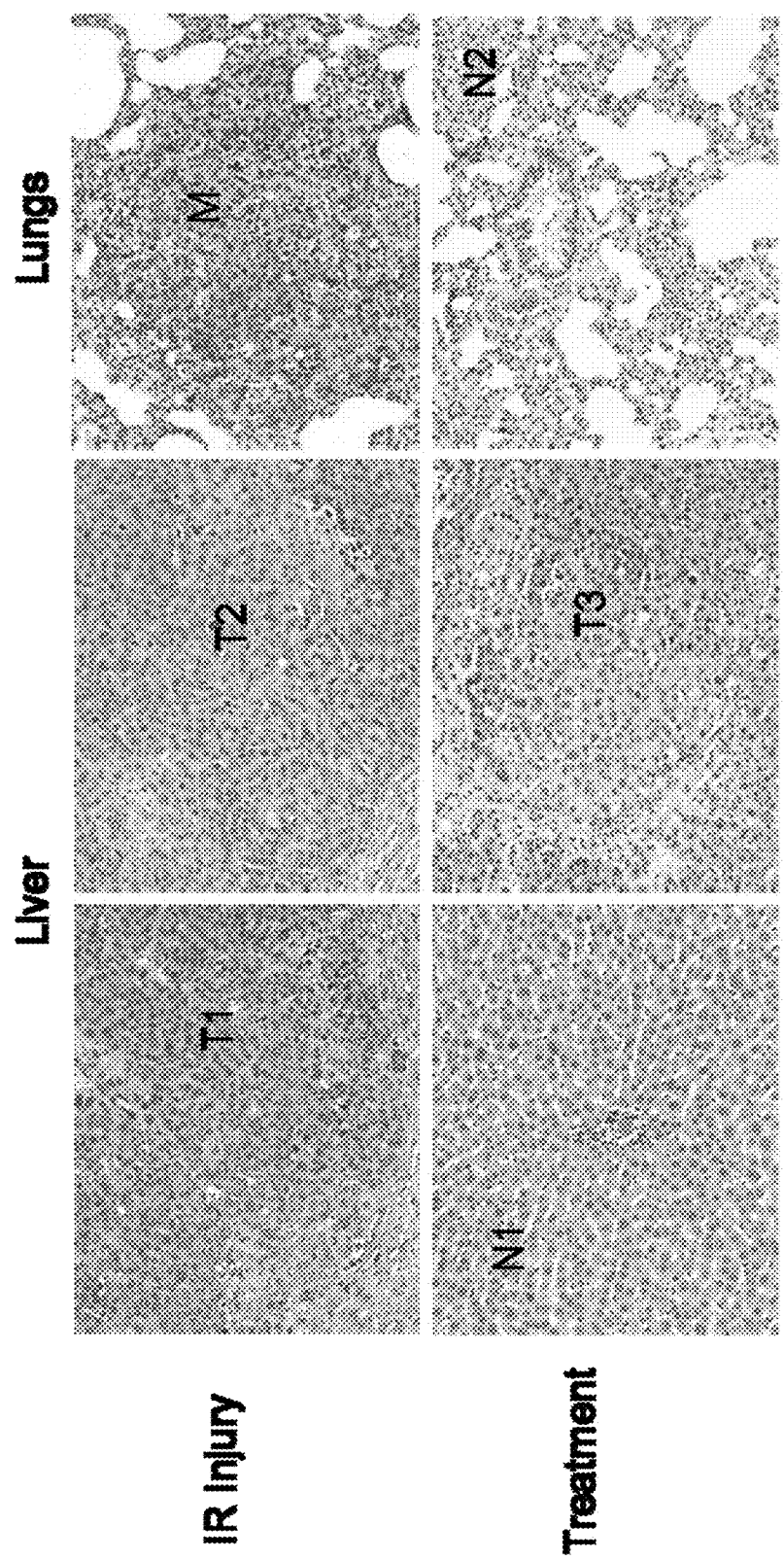
FIG. 19 shows the histological examination in experimental and control groups at four weeks after liver resection and IR injury procedures.

FIG. 19 shows the histological examination in both groups at four weeks after liver resection and IR injury procedures. Histological examination (H&E staining) of liver and lung tissues in both the IR injury and hemoglobin treatment groups is performed to confirm the identity of the tumor nodules. Representative fields showing intrahepatic recurrence (T1 and T2) and lung metastasis (M) in the IR injury group are shown (top). Histological examination showing a normal liver architecture in the treatment group (N1) and a tumor nodule detected in the liver after hemoglobin treatment (T3) are included for comparison (bottom). In addition, lung tissue without metastasis is shown in the treatment group (N2) for comparison.

To further confirm the protective effects of heat stable tetrameric hemoglobin on tumor recurrence and metastasis, recurrence rate of tumor and size of the recurred tumor post-ischemia/reperfusion and hepatectomy procedures are investigated. Again, rats with implanted tumor tissue prepared by injection of McA-RH7777 cells as described above are treated intravenously with either approximately 0.2-0.4 g/kg of the heat stable tetrameric hemoglobin of the present invention or Ringer's acetate (RA) buffer as a negative control prior to ischemia and at reperfusion upon hepatic resection procedure as described in FIG. 17. A total of 26 rats are tested, where 13 rats are treated with the subject hemoglobin and 13 are negative control rats which are merely treated with RA buffers. All rats are sacrificed 4 weeks after the hepatectomy and IR procedures, livers and lungs of the test rats are examined for tumor recurrence/metastasis and the relative size of the recurred tumors are measured.

Figure 20:
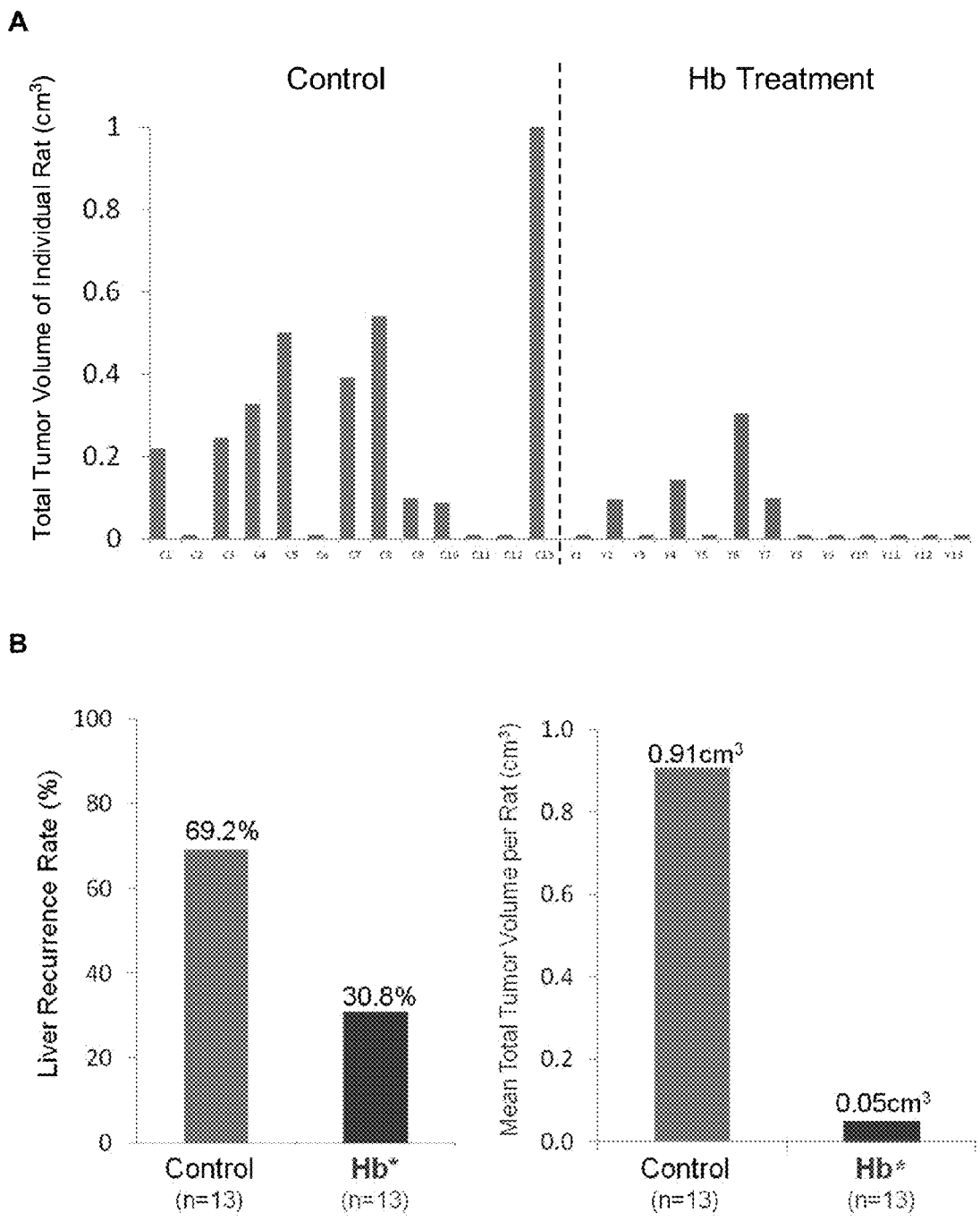
FIG. 20A shows the volume (cm$^3$) of recurred liver tumor found in rats of the IR injury group (Control group) after hepatectomy and IR procedures and rats having treated with the inventive heat stable tetrameric hemoglobin (Hb Treatment group).
FIG. 20B shows the liver recurrence rate (left) and the average recurred tumor size (right) of the IR injury rats after hepatectomy and IR procedures (Control group) and rats having treated with the inventive heat stable tetrameric hemoglobin (Hb group).

FIG. 20A shows liver tumor recurrence in test rats and the volume of individual recurred tumors. Liver tumor recurred/metastasis in 9 of the 13 non-treated control rats, whereas only 4 of the 13 treated rats experienced tumor recurrences/metastasis. It is also evident that where tumor recurrence is seen, the sizes of the recurred tumors of rats having treated with the subject hemoglobin are significantly smaller than those untreated. The results show that tumor recurrence rate is greatly reduced and recurred tumor size is significantly reduced with treatment of the subject invention, as summarized in FIG. 20B.

Figure 21:
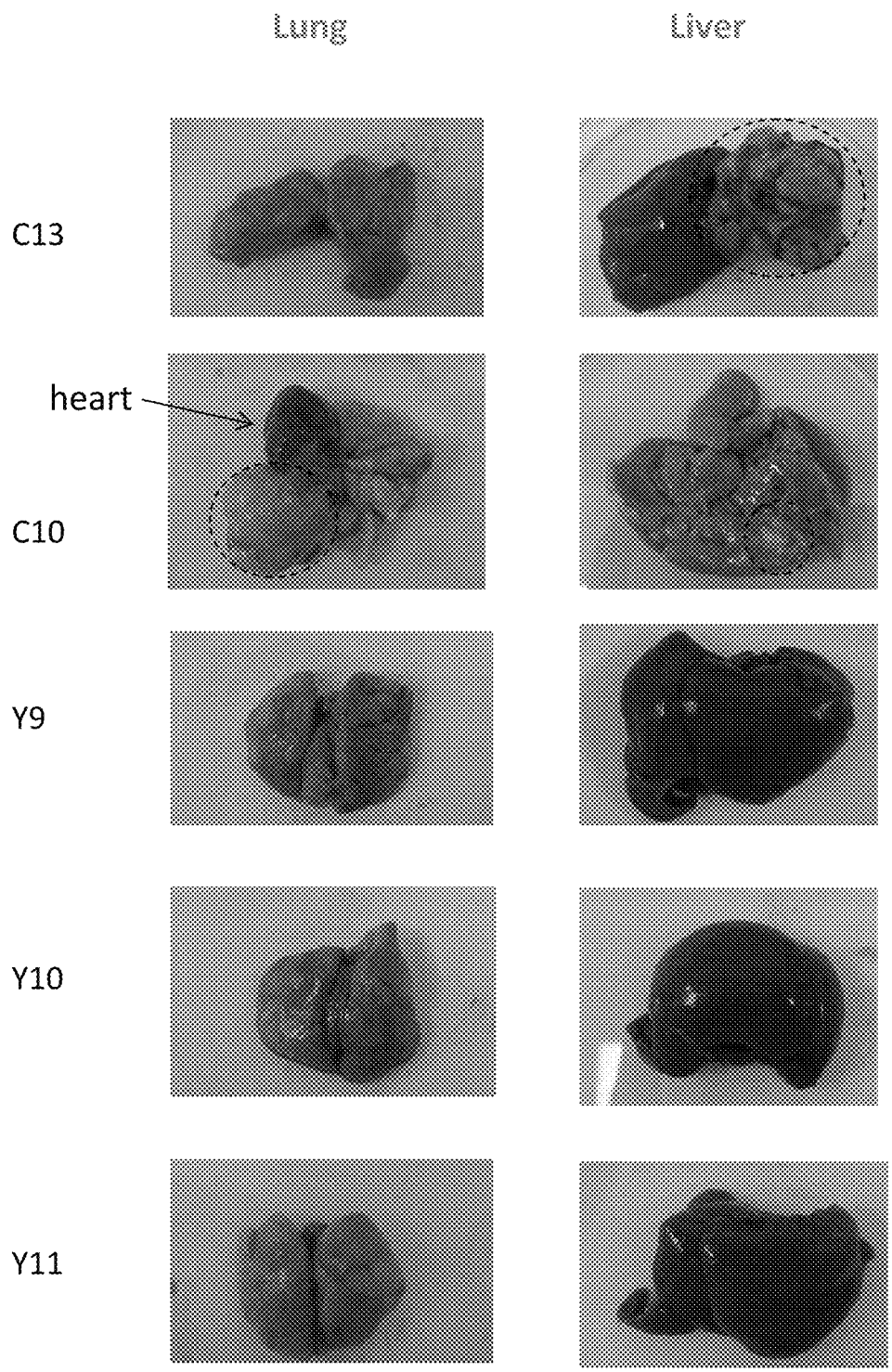
FIG. 21 shows representative examples of intra-hepatic liver cancer recurrence and metastasis and distant lung metastasis induced in the rats of the IR injury group after hepatectomy and ischemia/reperfusion procedures (control group: C10 & C13) and rats treated with the inventive heat stable tetrameric hemoglobin (Hb treatment group: Y9, Y10 & Y11).

FIG. 21 illustrates representative examples of liver and lung tissues harvested 4 weeks post hepatectomy and IR procedures of rats having treated with the subject inventive heat stable tetrameric hemoglobin and the IR injury (negative control) group. As seen in representative examples of the untreated negative control group, rats C10 and 13, extensive intrahepatic liver cancer recurrence/metastasis and distant lung metastasis are observed (circled). On the other hand, intrahepatic liver cancer recurrence/metastasis and distant lung metastasis are prevented by the treatment of the subject inventive hemoglobin, as seen in rats Y9, Y10 and Y11.

Example 10

Treatment with Heat Stable Tetrameric Hemoglobin Reduces Ischemia

Figure 22:
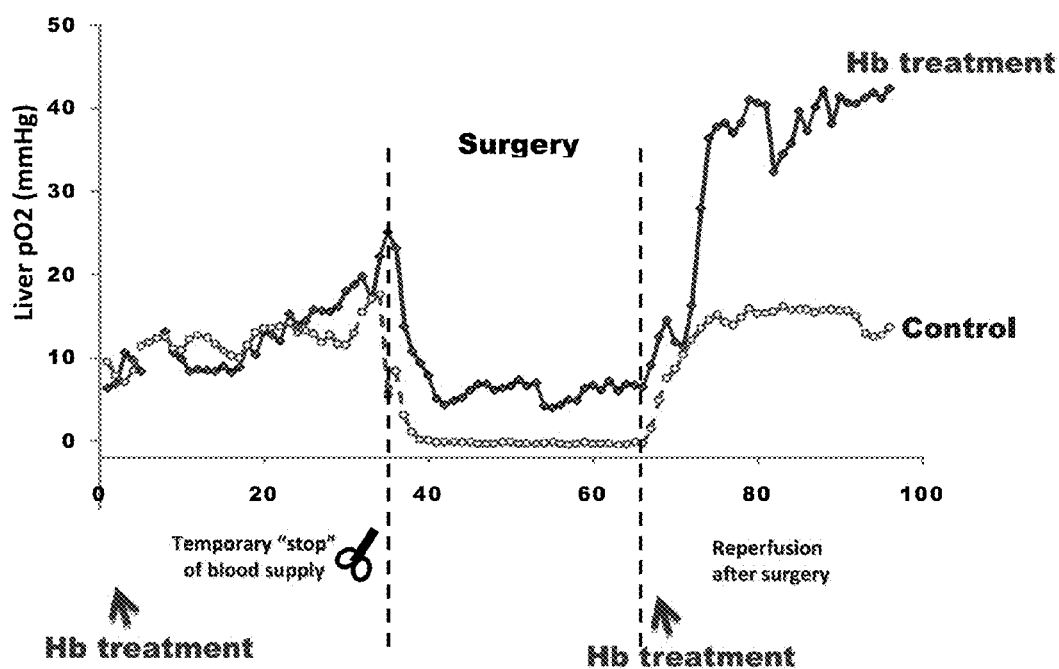
FIG. 22 shows the representative examples of liver oxygen partial pressure (mmHg) from the first administration of the subject inventive hemoglobin product or RA buffer (control) throughout the hepatic surgery and reperfusion.

As demonstrated in Example 6, intravenous injection of the subject heat stable tetrameric hemoglobin to hypoxic tumor significantly improves the oxygenation therein. Accordingly, the oxygenation effect of the subject hemoglobin product during tumor resection and IR procedure is investigated. Rats with implanted liver tumor tissue prepared by injection of McA-RH7777 cells are used and are subjected to surgery and 0.2-0.4 g/kg of the subject hemoglobin product or RA buffer administration procedures as outline in FIG. 17. Oxygen partial pressure of liver is measured from the time the subject hemoglobin product/RA buffer is first administered to the hepatic tumor and throughout the IR procedure, hepatic tumor resection and after reperfusion. Results (FIG. 22) shows that increased oxygenation with the subject hemoglobin treatment is observed after introduction of ischemia. In addition, as seen in FIG. 22, the liver having treated with the subject hemoglobin has approximately 3-fold higher oxygen partial pressure than without treatment after reperfusion. It is confirmed that the treatment of the subject hemoglobin prior to ischemia and at reperfusion upon tumor resection significantly improves the oxygenation of the liver tissue as compared to non-treatment. In view of the strong correlation between hypoxic tumor and the increased likelihood of tumor recurrences/metastasis suggested in the art, the profound oxygenation effects of the present hemoglobin product and the use thereof during tumor resection procedure as demonstrated in this example, the usefulness of the present hemoglobin product to reduce tumor recurrence and metastasis are evidently confirmed.

Example 11

Treatment with Heat Stable Tetrameric Hemoglobin Reduces Circulating Endothelial Progenitor Cell Levels Different lines of study have demonstrated the significance of cancer stem cells (CSCs) and/or progenitor cell populations in the progression of liver cancer Importantly, previous studies show that a significantly higher level of circulating endothelial progenitor cells (EPCs) is found in HCC patients, including those undergoing hepatectomy.

Figure 23:
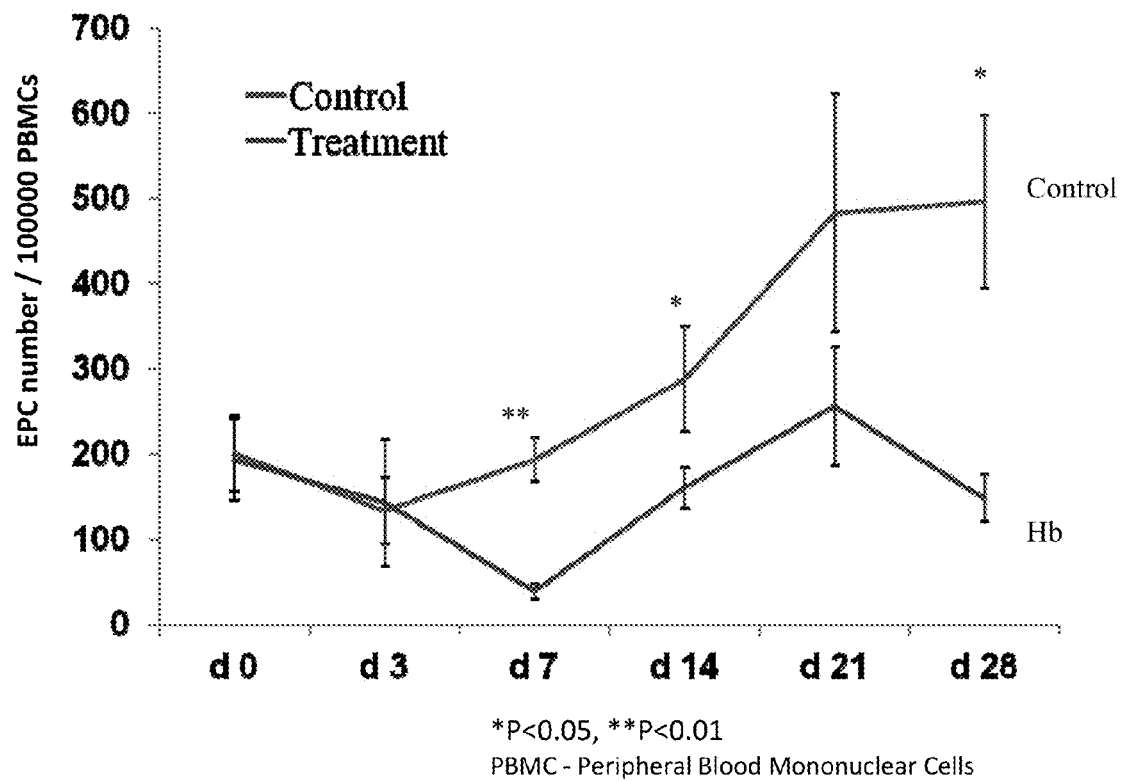
FIG. 23 shows a comparison between levels of circulating endothelial progenitor cells (EPC) in peripheral blood of rats with or without treatment of the subject hemoglobin product 28 days post-hepatic surgery.

Accordingly, the level of circulating EPCs is evaluated by expression of surface molecules such as CD133, CD34 and VEGFR2. The circulating endothelial progenitor cell levels post-hepatic resection surgery and IR procedure with or without the treatment of the subject hemoglobin product is investigated. Two groups of rats with implanted hepatic tumor are subjected to treatment of the subject hemoglobin or RA buffer (control), respectively prior to ischemia and at reperfusion upon hepatic resection as shown in FIG. 17. Number of circulating EPC of the two group of rats are then measured at 0, 3, 7 14, 21 and 28 days after hepatic resection and IR procedures. Results (FIG. 23) shows that while EPC levels of the treated and non-treated groups are comparable during day 0-day 3 post-surgery, EPC levels of the hemoglobin treated group are profoundly lower than those RA buffer treated group. The result shows that the protection effects of the subject hemoglobin can reduce and minimize tumor recurrence/metastasis.

Example 12

Localization of Heat Stable Tetrameric Hemoglobin within a Tumor Mass

Figure 24:
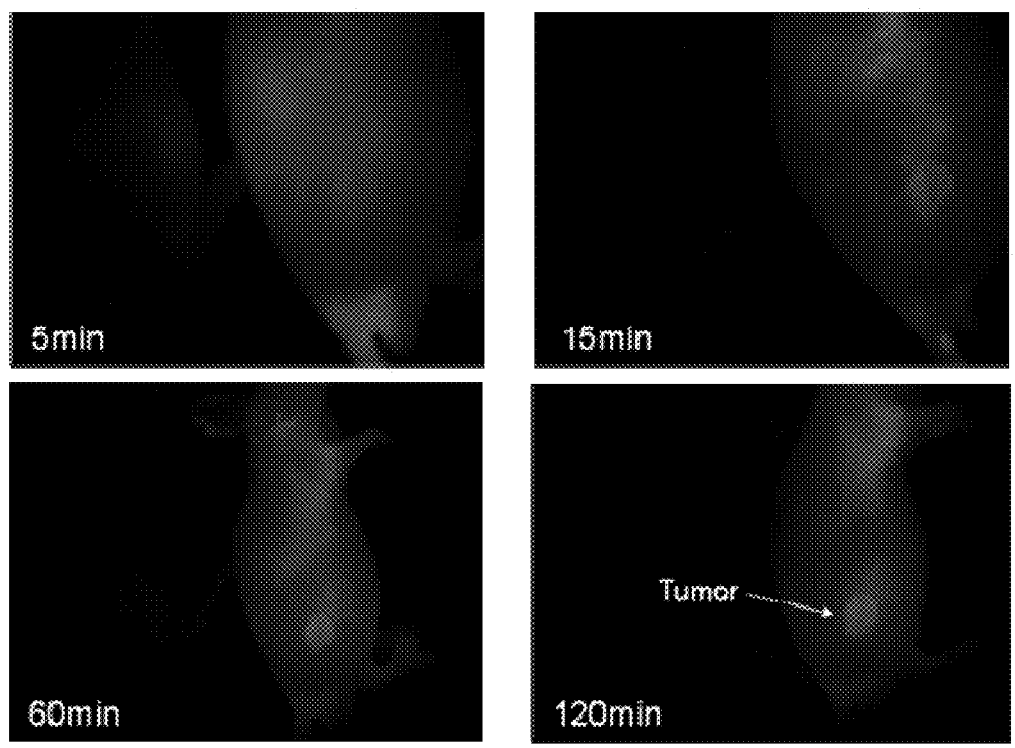
FIG. 24 shows the temporal localization of the heat-stable hemoglobin-based oxygen carrier within nasopharyngeal carcinoma Xenograft.

To visualize the localization of the heat stable tetrameric hemoglobin within the tumor mass, the inventive hemoglobin is labeled with Alexa Fluor® 750 SAIVI™ Antibody Labeling System according to manufacturer's instruction. Briefly, fluorescently labeled inventive hemoglobin (fl-Hb) is mixed with unlabeled counterpart in a ratio of approximately 1:80. The mixture is injected intravenously into nude mice bearing nasopharyngeal carcinoma xenograft (C666-1). For each nude mouse, the amount of fl-Hb is around 0.2 mg to ensure sufficient fluorescent signal to be captured by the Maestro2 imaging system. Nude mice are anesthetized at different time points before exposure to the Maestro2 fluorescent imaging system for analysis. FIG. 24 shows representative image of Hb concentrated within the tumor xenograft (indicated by an arrow).

Example 13

Figure 25:
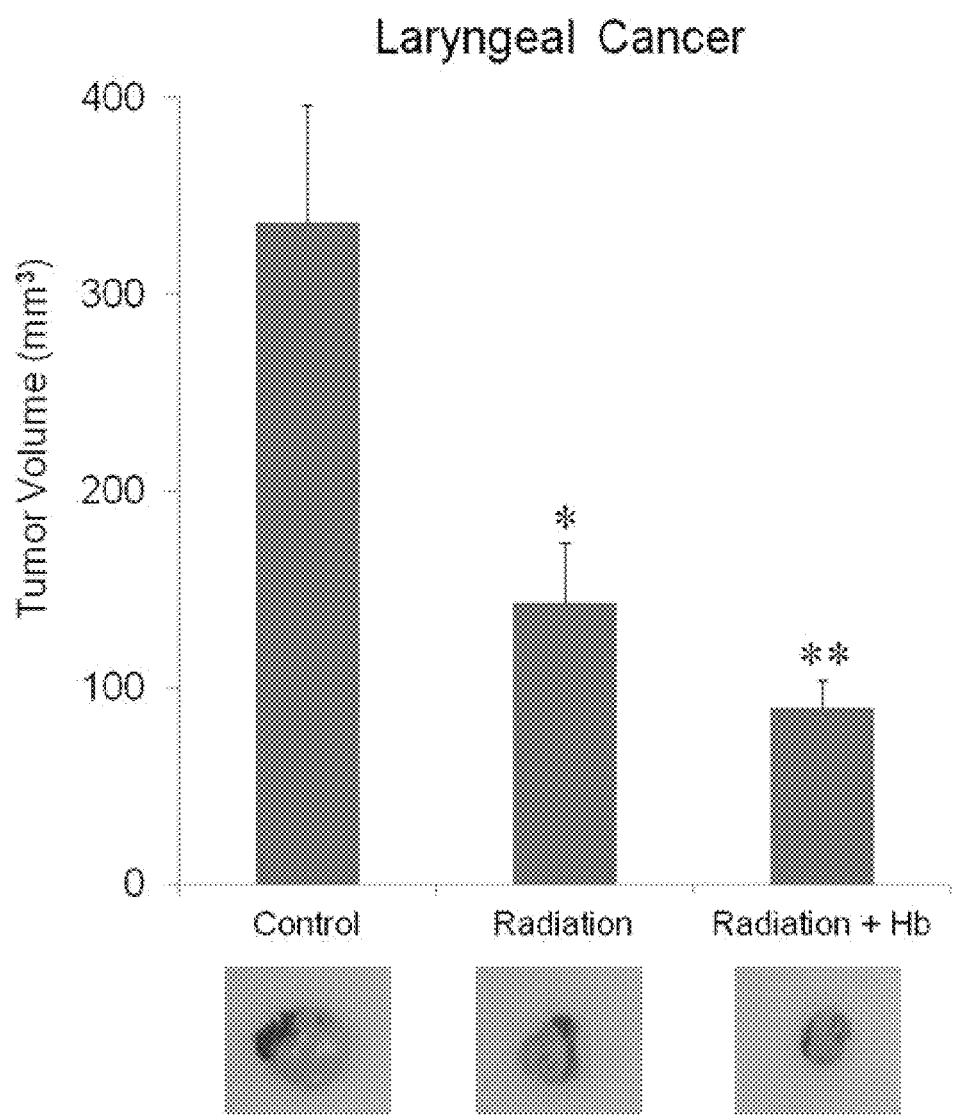
FIG. 25 shows the tumor growth inhibitory effect of the hemoglobin-based oxygen carrier alone or combined with radiation in a Hep-2 laryngeal cancer model; lower panel shows the representative image of tumor xenografts obtained from different treatment groups. *p<0.05, **p<0.01 versus control.

Radio-Sensitization Effects of the Heat Stable Tetrameric Hemoglobin in Laryngeal Cancers To evaluate the radio-sensitization effects of heat stable tetrameric hemoglobin in head and neck cancers, the hemoglobin-based oxygen carrier of the present invention is administered once before radiation, and the result shows that tumor growth inhibitory effects in the Hep-2 laryngeal cancer model. The tumor volume of high dose of Hb (2.2 g/kg) combined with radiation at the end of experiment is 90.0 $mm^3$, which is significantly smaller than the control group (336.1 $mm^3$) ($P<0.01$). The tumor volume of radiation alone is 143.1 $mm^3$, and the combination q value of administering a high dose of Hb is 1.17, indicating a synergistic effect of this combination ($q>1.15$, synergistic effect). FIG. 25 shows the tumor growth inhibition effects of the hemoglobin-based oxygen carrier of the present invention followed by radiation.

Example 14

Figure 26:
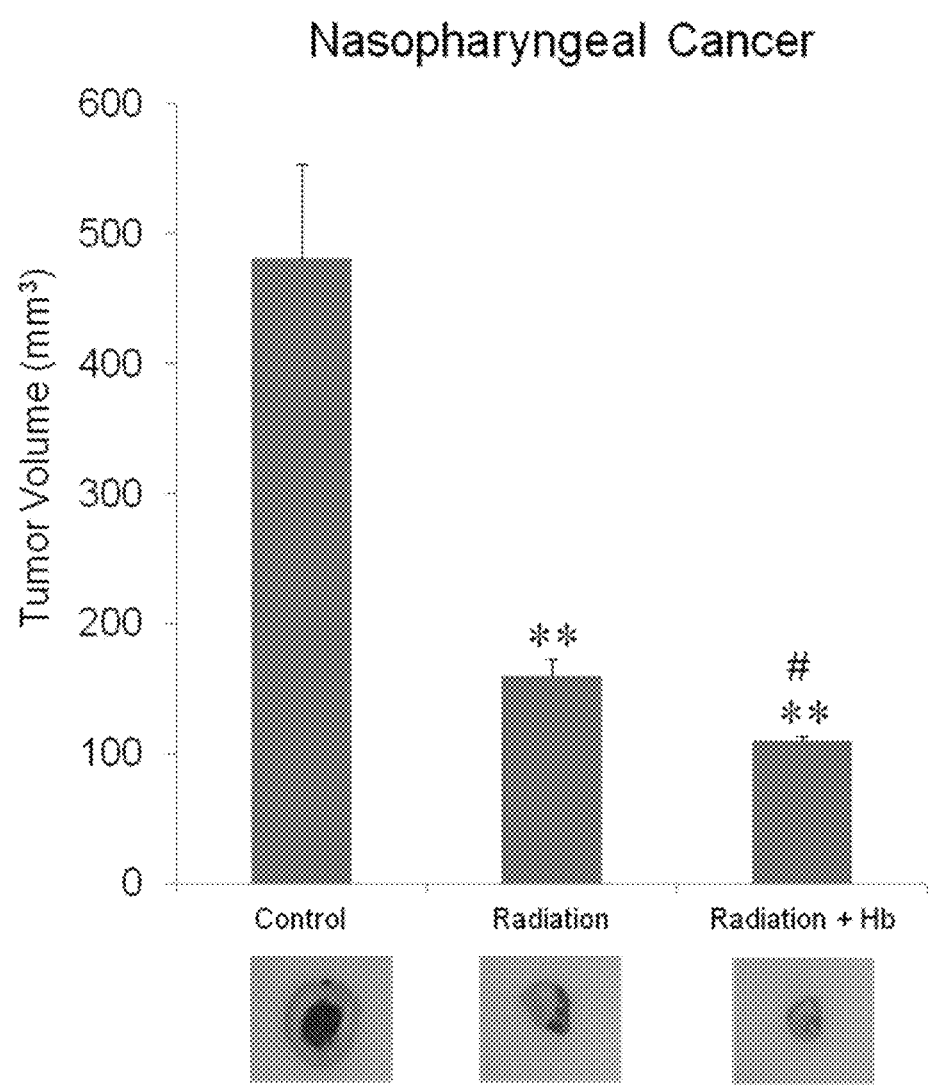
FIG. 26 shows the tumor growth inhibitory effect of the hemoglobin-based oxygen carrier combined with radiation in a C666-1 nasopharyngeal cancer model; lower panel shows representative image of tumor xenografts obtained from different treatment groups. **p<0.01 versus control, #p<0.05 versus radiation treatment only.

Radio-Sensitization Effects of Heat Stable Tetrameric Hemoglobin in Nasopharyngeal Cancer To evaluate the radio-sensitization effects of heat stable tetrameric hemoglobin in nasopharyngeal cancer, the hemoglobin-based oxygen carrier of the present invention is administered once before radiation, and the result shows that tumor growth inhibitory effect in the C666-1 nasopharyngeal cancer model. The tumor volume of high dose of Hb (2.2 g/kg) combined with radiation at the end of experiment is 110.3 $mm^3$, which is significantly smaller compared with the control group (481.1 $mm^3$) ($P<0.01$), and also significantly smaller compared with the radiation alone group (160 $mm^3$) ($P<0.05$). The combination q value of Hb high dose is 1.24, indicating a synergistic effect of this combination ($q>1.15$, synergistic effect). FIG. 26 shows the tumor growth inhibition effects of the hemoglobin-based oxygen carrier of the present invention followed by radiation.

Example 15

Chemo-Sensitization Effects of the Heat Stable Tetrameric Hemoglobin in Brain Cancer Glioblastoma multiforme (GBM) is the commonest type of primary brain tumor in adults and one of the most aggressive and lethal malignancies in human, it is characterized by rapid growth, invasiveness and early recurrences. The prognosis of GBM patients is extremely unfavorable with a median survival of approximately 1 year. Although the alkylating agent temozolomide (TMZ) can significantly prolong survival, most patients develop tumor recurrences due to de novo or acquired TMZ-resistance.

Accordingly, the sensitization effect of Hb on temozolomide-induced cytotoxicity in glioblastoma multiforme is studied. GBM cells sensitive (D54-S) and resistant (D54-R) to temozolomide are treated with various concentration (0.015 to 0.03 g/dL) of Hb alone, TMZ alone or in combination under hypoxia (1% oxygen) for 72 hours followed by cell viability assays.

Figure 27:
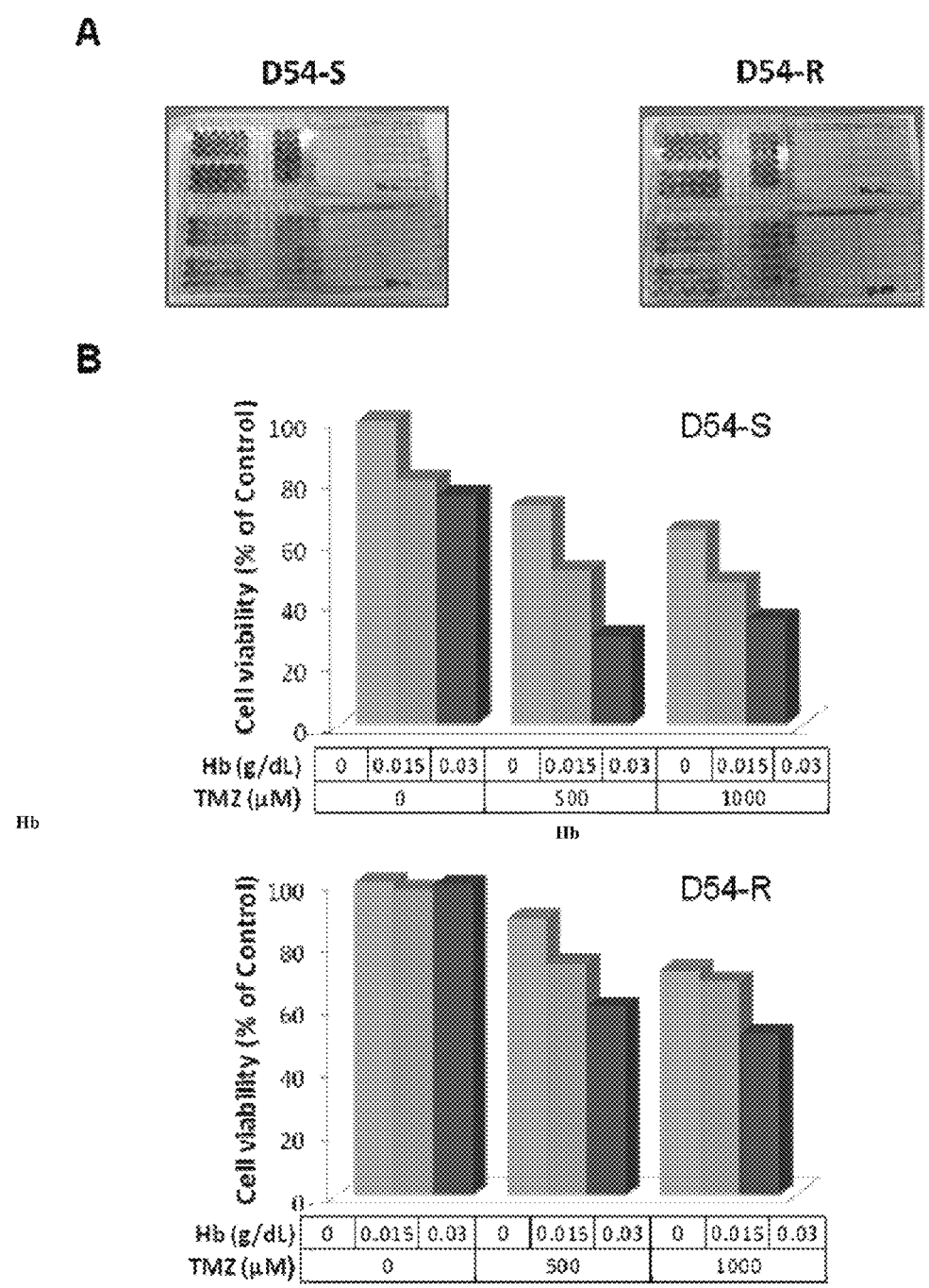
FIG. 27 shows the hemoglobin-based oxygen carrier enhances temozolomide (TMZ)-induced cytotoxicity in brain cancer cells.

Results show that Hb enhances TMZ-induced cytotoxicity in both D54-S and D54-R GBM cells in vitro. FIG. 27A shows representative 96-well plates of D54-S and D54-R cells after different treatment conditions. FIG. 27B shows a dose-dependent enhancement of TMZ-induced cytotoxicity by Hb.

Example 16

Isolation of Cancer Stem Cells by Flow Cytometry

A breast cancer cell line, MCF7 cells, is labelled with CD24 and CD44 antibodies and analyzed by flow cytometry using PE and APC isotypes which are excited by 488 nm (blue laser) and 633 nm (red laser), respectively, and the respective emissions are measured by 585 nm and 660 nm Band Pass filters. The flow cytometry result shows that the percentage of the commercially available MCF7 cells which highly express CD44 but not CD24 is only about 0.5% in the total population.

Figure 28:
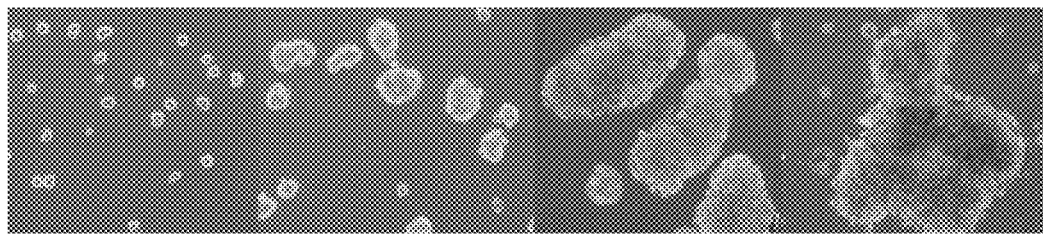
FIG. 28 are microscopic images showing the morphological change of mammospheres formation by cancer stem cells: (A) Day 0, (B) Day 3, (C) Day 6, (D) Day 9-20, (E) Control (hollow mammospheres from mammary epithelial cells).
Figure 28:
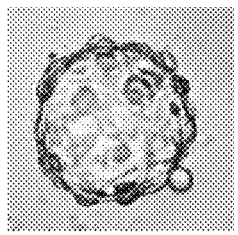
Figure 29:
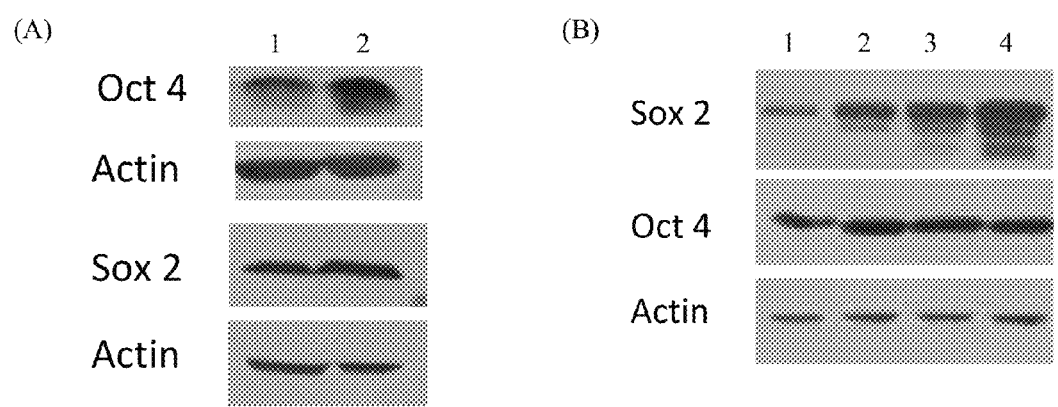
FIG. 29 are western blots showing the expression level of different markers Oct-4 and Sox-2 in unsorted mammospheres and sorted MCF7 CD44$^+$/CD24$^-$ cells collected from different passages.

In order to obtain the desired cancer stem cells, MCF7 cells are cultured in suspension on non-coated petri dishes in MammoCult™ for at least 7-9 days before spheroids formation. The culture medium contains both MammoCult Basal Medium and MammoCult Proliferation Supplement for human mammospheres. The culture medium is also supplemented with 0.48 μg/mL freshly dissolved hydrocortisone and 4 μg/mL heparin before use. The culture medium in the petri dishes is changed every 1-2 days and the frequency can be determined from the color of the medium. The morphology of the cell is observed under microscope. FIG. 28 shows the cell morphology observed in the phase contrast field under a light microscope. As compared to the hollow mammospheres derived from mammary epithelial cells (E, Control), solid mammospheres are observed at about $9^{th}$ to $20^{th}$ days of growth after pouring the flow-sorted MCF7 cells onto the petri dishes. The self-renewal ability is further confirmed by passing the cancer stem cells for about 9 passages and each subsequent passage after passage 0 may take about 9-14 days to develop into solid mammospheres. From one passage to the other, the solid mammospheres are separated into single cells by chemical (e.g. trypsinization) or mechanical means in a sterile environment (e.g. using cell scraper to detach the cell clump from the Petri dish followed by pipetting up and down). Single cells from each passage are collected for further protein analysis to confirm the identity and self-renewal ability of the cancer stem cells. FIG. 29 shows western blots of lysed cells collected in different passages. In FIG. 29A, sample 1 is for unsorted cells from mammospheres and sample 2 is for CD44+/CD24- sorted cells from mammospheres at passage 1. In FIG. 29B, sample 1 is for unsorted cells from mammospheres and samples 2, 3 and 4 are for CD44+/CD22- sorted cells from mammospheres at passage 1, 2 and 3, respectively. From the western blot, both unsorted and sorted cells from mammospheres are shown to express the stem cell marker Oct-4 (39 kDa) and Sox-2 (40 kDa). However, the expression level of these markers between unsorted and sorted cells is different. Obviously, the CD44+/CD24- sorted cells have higher expression level of Oct-4 than that of unsorted cells in the same passage. The self-renewal ability of the cancer stem cells becomes higher in terms of the expression level of these stem cells markers from one passage to another because of the application of cell sorting in each passage to select CD44+/CD24- cells.

Figure 30:
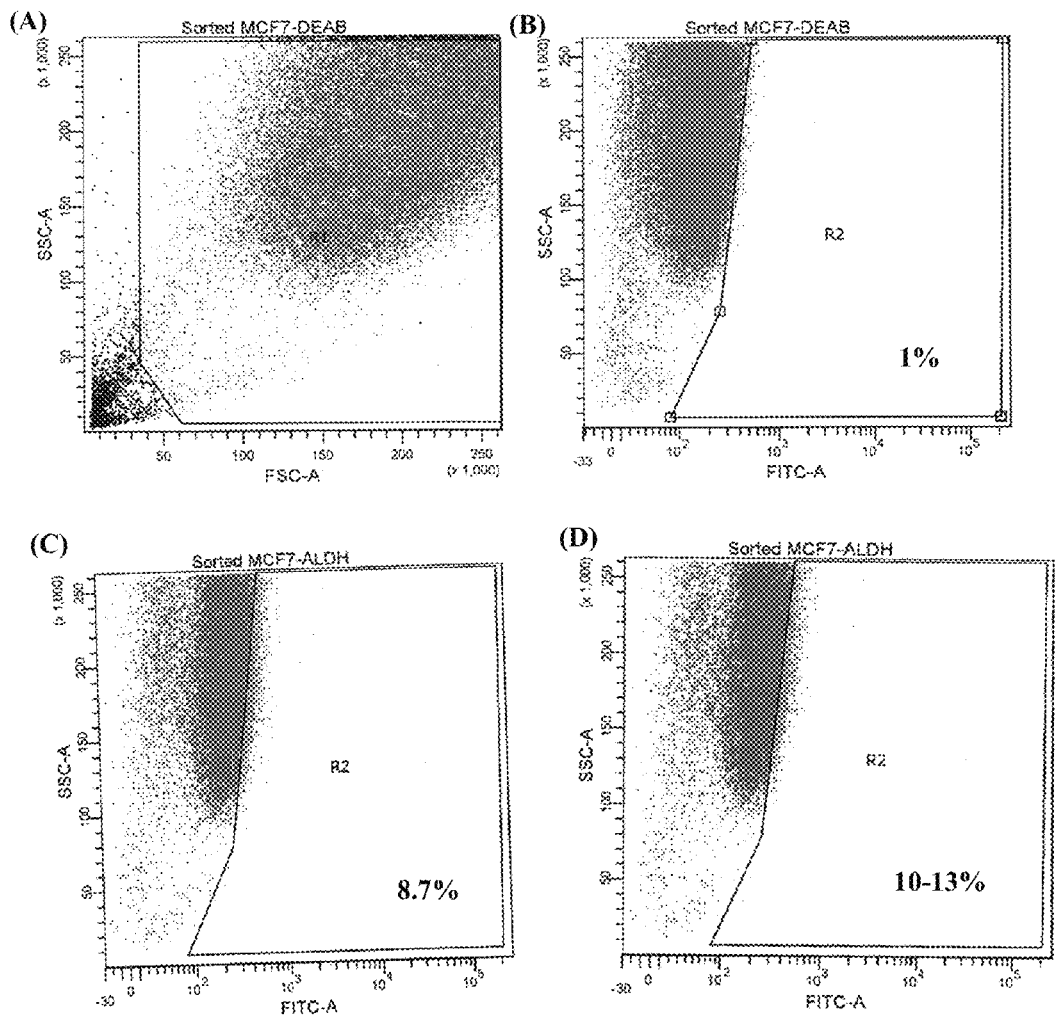
FIG. 30 are dot plots of different passages of MCF7 cells in terms of the aldehyde dehydrogenase (ALDH) activity: (A) Control (sorted MCF7 cells incubated with diethylaminobenzaldehyde (DEAB)); (B) sorted MCF7 cells at passage 0; (C) sorted MCF7 cells at passage 3; (D) sorted MCF7 cells at passage 5.

To further examine the tumor-initiating ability of the cancer stem cells, aldehyde dehydrogenase (ALDH) activity is studied by labelling the collected cells from mammospheres at different passages with ALDH-antibody and analyzing the labelled cells with the flow cytometry. FIG. 30A is the result of the analysis on a control (cells incubated with diethylaminobenzaldehyde (DEAB), an inhibitor of ALDH); FIG. 30B is the result of cells collected at passage 0, where it shows 1% of the cell population having the ALDH activity; FIG. 30C is the result of the cells collected at passage 3, where it shows about 8.7% of the cell population having ALDH activity; cells collected at passage 5 have about 10-13% of the population having ALDH activity (FIG. 30D). In this analysis, it demonstrates that the cells isolated from mammosphere have tumor-initiating and self-renewal abilities while become more dominant in the cell population of the cancer cells under the selective pressures from passage to passage. It also coincides with the previous studies on the cancer stem cells.

Example 17

Effect of Hemoglobin-Based Oxygen Carrier on Cancer Stem Cells

Figure 31:
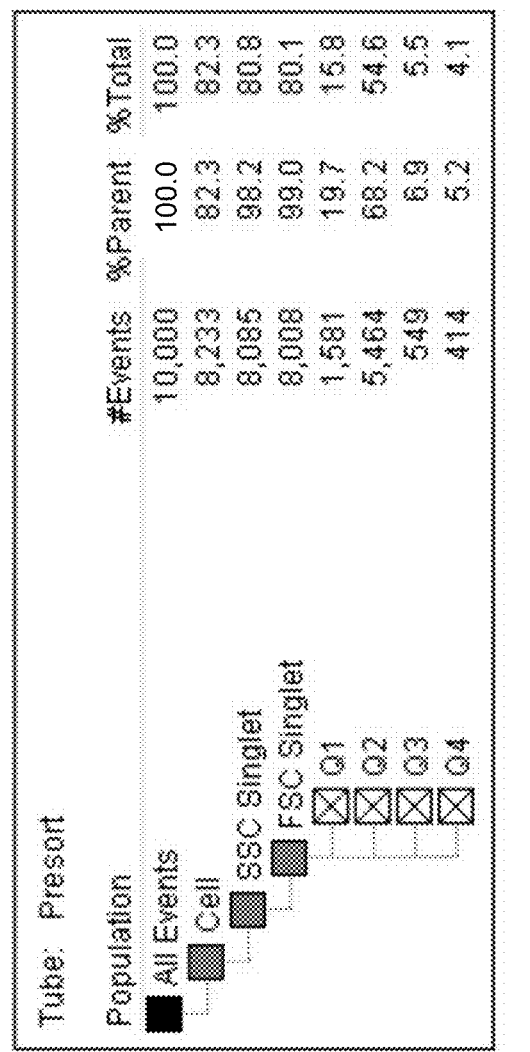
FIG. 31 is dot plots of MCF7 cells under hypoxic conditions and labeled with CD24 (PE-A) and CD44 (APC-A) antibodies in a flow cytometry analysis. Quadrant 1 (Q1) are cells which are CD44$^{high}$ and CD24$^{low}$.
Figure 31:
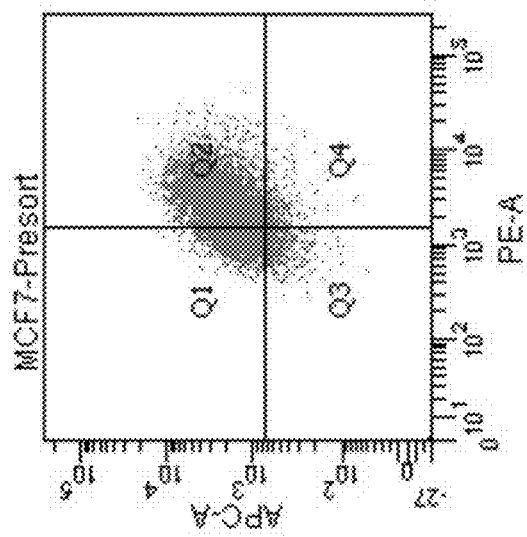

In order to test the effect of hemoglobin-based oxygen carrier on the cancer stem cells in a tumor, the MCF7 cells are incubated under hypoxic condition (5% $CO_2$ and 1.1% $O_2$) for 9-20 days before passing to the cell sorter where two filters are used: PE-A for CD24 marker while APC-A for CD44 marker. Quadrant 1 where cells are positive to CD44 and negative to CD24 (FIG. 31) are sorted for further analysis.

Figure 32:
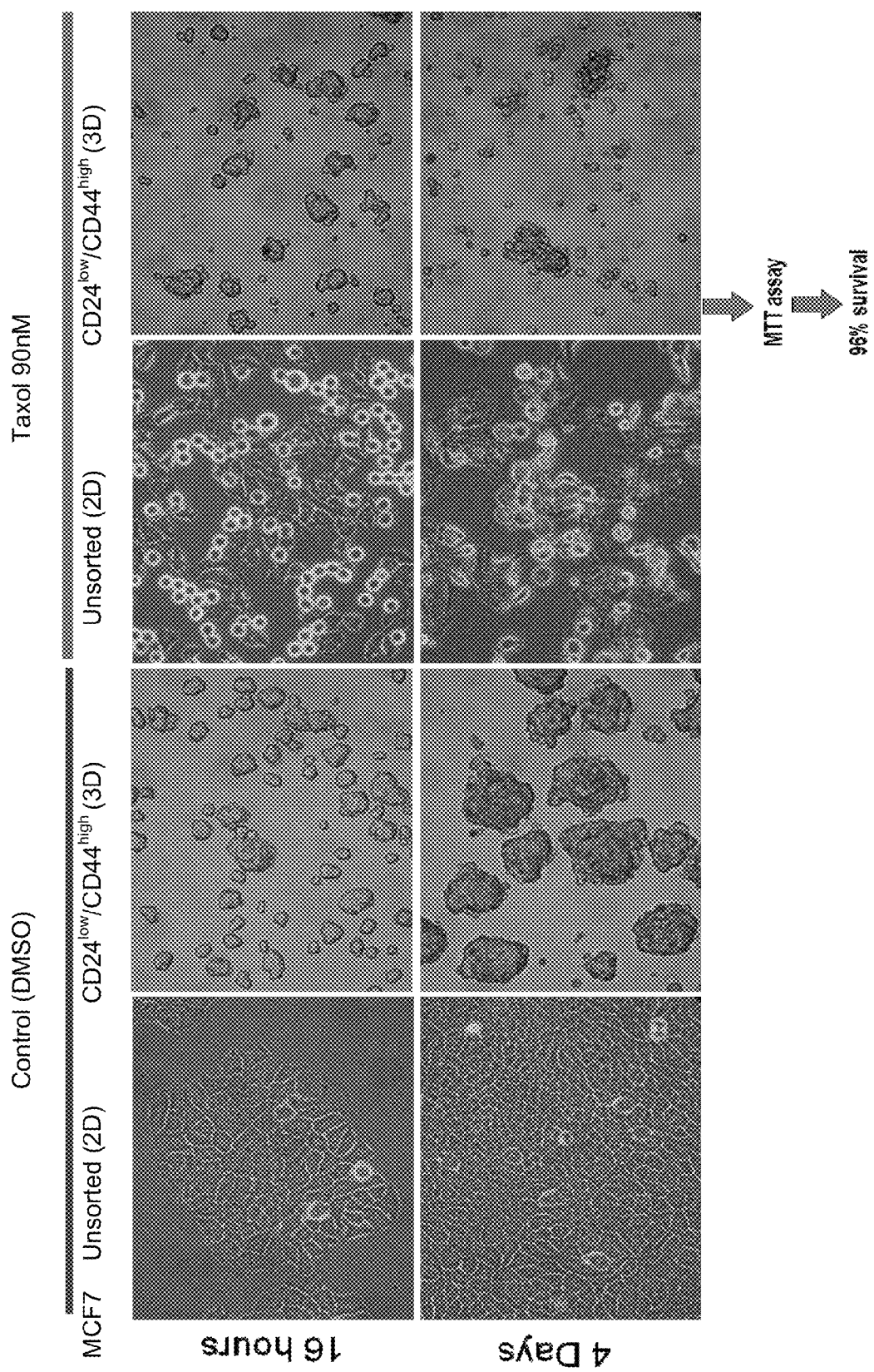
FIG. 32 are microscopic images showing the morphological change of unsorted and CD24/CD44-sorted MCF7 cells after incubated with DMSO (Control) and 90 nM Taxol treatment for 16 hours and 4 days.

To test sensitivity of the cancer stem cells to chemotherapeutic agent alone or to the combined therapy of hemoglobin-based oxygen carrier and the chemotherapeutic agent, different sets of chemotherapeutic agent and/or the hemoglobin-based oxygen carrier of the present invention are administered to MCF7 cells isolated from mammospheres which are obtained at later passages, e.g. passages 7 and 8. Before testing the sensitivity of the cancer stem cells, the drug resistance of CD44+/CD24- to chemotherapeutic agent is shown in FIG. 32. Unsorted MCF7 cells and CD44+/CD24- sorted cells are incubated with DMSO (as control) and 90 nM of Taxol for 16 hours and 4 days. Phase contrast images (FIG. 32) for each set of sample are taken at each time interval (16 hours and 4 days) and the sorted cells after Taxol treatment for 4 days are further tested by MTT assay (as described in Example 3) to confirm the drug resistance of these cells to chemotherapeutic agent. From the cell morphology, the mammosphere formation of both unsorted and CD44+/CD24- sorted cells seem to be inhibited by Taxol at 90 nM. However, the MTT assay of the sorted cells after treatment with Taxol for 4 days shows about 96% survival, which means that the CD44+/CD24- sorted cells possess high resistance to Taxol alone.

The high resistance of the CSCs to chemotherapeutic agent is further confirmed by the results of MTT assays on single cells from two passages (P7 and P8) after the mammospheres are treated with different combination of chemical(s) for at least 24 hours before trypsinization of mammospheres. The mammospheres are grown under the hypoxic conditions (5% $CO_2$, 1.1% $O_2$) to mimic the physiological environment of a tumor. Different combination of chemical(s) used in the MTT assays include the Hb alone (0.2 g/dL), Bortezomib ("Bort", 0.5 µM) alone, 5-fluorouracil ("5FU", 5 µM) alone, or any combination of the above. In case of the combinational drug (i.e. Hb+at least one chemotherapeutic agent), the trypsinized cells are incubated with 0.2 g/dL of Hb for 24 hours followed by the addition of the intended chemotherapeutic agent(s) and incubated for another 24 hours. The absorbance is measured by the spectrometer and the normalized value of the absorbance is given in Table 3 below. In the normalized value, "1" represents 100% of survival rate; 0.75 represents 75% of survival rate, etc.

In the set of administering 0.2 g/dL of Hb only, the survival rate of cells from two passages is about 61-65% survival rate. In the set of administering 0.5 µM of Bortezomib alone, cells from two passages have about 78%-91% survival rate. In the set of administering 5 µM of 5FU alone, cells from two passages have about 72%-87% survival rate. In the set of administering 0.2 g/dL of Hb+0.5 µM of Bortezomib, the survival rate of cells from two passages is about 38%-49%. In the set of administering 0.2 g/dL of Hb+5 µM of 5FU, the survival rate of cells from two passages is about 52%-72%. In the set of administering 0.5 µM of Bortezomib and 5 µM of 5FU, the survival rate of cells from two passages is about 60%-64%. In the set of administering 0.2 g/dL of Hb+0.5 µM of Bortezomib and 5 µM of 5FU, the survival rate of cells from two passages is about 33%-39%. By comparing the set of administering one chemotherapeutic agent alone and the combination of the hemoglobin-based oxygen carrier and the same agent, the survival rate is decreased almost by half in the case of Bortezomib; the survival rate is decreased by about 17% to 20% in the case of 5FU. Although the survival rate of the cells in the combination of Bortezomib and 5FU is about 60%-64%, it is still comparatively higher than that of the cells treated with the hemoglobin-based oxygen carrier and Bortezomib. It is interesting to note that hemoglobin-based oxygen carrier alone can kill the CSCs by almost the same percentage as that of using the combination of Bortezomib and 5FU. Finally, the most effective combination of killing the CSCs in this test is the hemoglobin-based oxygen carrier plus Bortezomib and 5FU because the survival rate is only about 33%-39% which is far lower than any of the other combination as described herein. However, it should be noted that the chemotherapeutic agent administered in combination with the hemoglobin-based oxygen carrier of the present invention is not limited to Bortezomib or 5FU. Any other conventional chemotherapeutic agents which have been proven to be less effective in treating cancer/tumor or any other therapy such as radiotherapy can also be used in combination with the hemoglobin-based oxygen carrier of the present invention with an improved efficacy in killing CSCs.

TABLE 3

| Mammosphere (P7) under Hypoxic condition | | | | | | | | | | | | |
|---|---|---|---|---|---|---|---|---|---|---|---|---|
| | Absorbance | | | | | Avg | Normalized | | | | | Avg |
| Control | 0.167 | 0.188 | 0.217 | 0.191 | 0.182 | 0.189 | 0.883598 | 0.994709 | 1.148148 | 1.010582 | 0.962963 | 1 |
| Hb only | 0.114 | 0.126 | 0.128 | 0.118 | 0.132 | | 0.603175 | 0.666667 | 0.677249 | 0.624339 | 0.698413 | 0.653968 |
| Bort 0.5 μM | 0.178 | 0.172 | 0.177 | 0.163 | 0.174 | | 0.941799 | 0.910053 | 0.936508 | 0.862434 | 0.920635 | 0.914286 |
| Hb + Bort 0.5 μM | 0.091 | 0.077 | 0.089 | 0.105 | 0.101 | | 0.481481 | 0.407407 | 0.470899 | 0.555556 | 0.534392 | 0.489947 |
| 5FU 5 μM | 0.171 | 0.197 | 0.139 | 0.143 | 0.169 | | 0.904762 | 1.042328 | 0.73545 | 0.756614 | 0.89418 | 0.866667 |
| Hb + 5FU 5 μM | 0.126 | 0.144 | 0.141 | 0.135 | 0.137 | | 0.666667 | 0.761905 | 0.746032 | 0.714286 | 0.724868 | 0.722751 |
| Bort 0.5 μM + 5FU 5 μM | 0.126 | 0.112 | 0.117 | 0.129 | 0.121 | | 0.666667 | 0.592593 | 0.619048 | 0.68254 | 0.640212 | 0.640212 |
| Hb + Bort 0.5 μM + 5FU 5 μM | 0.071 | 0.071 | 0.079 | 0.079 | 0.069 | | 0.375661 | 0.375661 | 0.417989 | 0.417989 | 0.365079 | 0.390476 |

| Mammosphere (P8) under Hypoxic condition | | | | | | | | | | | |
|---|---|---|---|---|---|---|---|---|---|---|---|
| | Absorbance | | | | | Avg | Normalized | | | | Avg |
| Control | 0.244 | 0.183 | 0.22 | 0.189 | 0.209 | | 1.167464 | 0.875598 | 1.052632 | 0.904306 | 1 |
| Hb only | 0.139 | 0.125 | 0.127 | 0.122 | | | 0.665072 | 0.598086 | 0.607656 | 0.583732 | 0.613636 |
| Bort 0.5 μM | 0.169 | 0.166 | 0.159 | 0.155 | | | 0.808612 | 0.794258 | 0.760766 | 0.741627 | 0.776316 |
| Hb + Bort 0.5 μM | 0.084 | 0.062 | 0.087 | 0.082 | | | 0.401914 | 0.296651 | 0.416268 | 0.392344 | 0.376794 |
| 5FU 5 μM | 0.155 | 0.165 | 0.129 | 0.157 | | | 0.741627 | 0.789474 | 0.617225 | 0.751196 | 0.72488 |
| Hb + 5FU 5 μM | 0.112 | 0.111 | 0.102 | 0.108 | | | 0.535885 | 0.5311 | 0.488038 | 0.516746 | 0.517943 |
| Bort 0.5 μM + 5FU 5 μM | 0.122 | 0.129 | 0.127 | 0.124 | | | 0.583732 | 0.617225 | 0.607656 | 0.593301 | 0.600478 |
| Hb + Bort 0.5 μM + 5FU 5 μM | 0.069 | 0.063 | 0.076 | 0.064 | | | 0.330144 | 0.301435 | 0.363636 | 0.30622 | 0.325359 |

If desired, the different functions discussed herein may be performed in a different order and/or concurrently with each other. Furthermore, if desired, one or more of the above-described functions may be optional or may be combined.

As a result of the above investigations, it is concluded that treatment with the heat stable tetrameric hemoglobin of the present invention has a preventative effect on both the recurrence of hepatic tumors and on metastasis in other organs.

While the foregoing invention has been described with respect to various embodiments, such embodiments are not limiting. Numerous variations and modifications would be understood by those of ordinary skill in the art. Such variations and modifications are considered to be included within the scope of the following claims.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes exemplary embodiments of the invention, these descriptions should not be viewed in a limiting sense. Rather, there are several variations and modifications which may be made without departing from the scope of the present invention as defined in the appended claims

What is claimed is:

1. A method for reducing recurrence of cancerous tumors and minimizing local and distant metastasis comprising administering a composition comprising a hemoglobin-based oxygen carrier at a concentration of 9.5 to 10.5 g/dL in combination with at least one chemotherapeutic agent or radiotherapy to facilitate uptake and localization of the hemoglobin-based oxygen carrier into cancer cells within a mass of cancerous tissues or tumors for inducing apoptosis in cells of said cancerous tissues or tumors including self-renewing and tumor-initiating cells, providing oxidative stress or shock to said cancerous tissues or tumors, and sensitizing the cancerous tissues or tumors to the at least one chemotherapeutic agent or radiotherapy, said composition being either administered to a subject in need thereof concurrently with or subsequently to the at least one chemotherapeutic agent.

2. The method of claim 1, wherein said composition is administered to said subject during or after removal of the cancerous tissues or tumors.

3. The method of claim 1, wherein the cancerous tissues or tumors are hypoxic.

4. The method of claim 3, wherein the hypoxic cancerous tissues or tumors comprise hepatic, nasopharyngeal, brain, colon, lung, head and neck, mammary and leukemia.

5. The method of claim 1, wherein said hemoglobin-based oxygen carrier is selected from modified or recombinant hemoglobin molecule which is either chemically conjugated with or surface modified with at least one compound.

6. The method of claim 5, wherein said hemoglobin-based oxygen carrier is cross-linked tetrameric hemoglobin having a molecular weight of 60-70 kDa and is heat stable after heat treatment and addition of N-acetyl cysteine at a concentration of 0.05-0.4% and said at least one compound is the chemotherapeutic agent.

7. The method of claim 6, wherein said composition is non-pyrogenic, endotoxin-free, phospholipid-free, stroma-free and has a met-hemoglobin level of less than 5% after said heat treatment and reaction with the added N-acetyl cysteine.

8. The method of claim 1, wherein said composition is administered by infusion or intravenous injection of the hemoglobin-based oxygen carrier in a range of approximately 0.2-1.2 g/kg body weight of the subject.

9. The method of claim 1, wherein said at least one chemotherapeutic agent is selected from 5-fluorouracil, doxorubicin, cisplatin, or any combination thereof.

10. The method of claim 1, wherein said hemoglobin-based oxygen carrier and at least one chemotherapeutic agent are administered concurrently to synergistically target cells with expression of a receptor in said cancerous tissues or tumors, thereby triggering a receptor-mediated mechanism, and sensitizing the cells in the cancerous tissues or tumors such that more hemoglobin-based oxygen carriers and chemotherapeutic agent are selectively taken up by the cells and localized in the cytoplasm of the cells while said cells become more sensitive to said chemotherapeutic agent.

11. The method of claim 1, wherein said hemoglobin-based oxygen carrier is administered to said subject as an adjunctive therapy subsequently to said at least one chemotherapeutic agent for providing oxidative stress or shock to a mass of the cancerous tissues or tumors and for sensitizing said cancerous tissues or tumors to said chemotherapeutic agent such that apoptosis of cells in said cancerous tissues or tumors including self-renewing and tumor-initiating cells is induced.

12. The method of claim 1, wherein said self-renewing and tumor-initiating cells comprise cancer stem cells and/or cancerous progenitor cells.

13. The method of claim 10, wherein said receptor-mediated mechanism is Clathrin-mediated endocytosis or said receptor is Clathrin.

14. The method of claim 5, wherein said at least one compound is poly(ethylene) glycol.

15. The method of claim 10, wherein said hemoglobin-based oxygen carrier is chemically conjugated with the chemotherapeutic agent in order to have the synergic effects on cancerous tissues or tumors.

16. The method of claim 3, wherein said hemoglobin-based oxygen carrier inhibits expression of hypoxic response elements comprising HIF1α, VEGF, ET1, and VHL in the hypoxic cancerous tissues or tumor.

* * * * *